US010220045B2

(12) United States Patent
Darien et al.

(10) Patent No.: US 10,220,045 B2
(45) Date of Patent: Mar. 5, 2019

(54) COMPOSITIONS AND METHODS FOR FORMING STABILIZED COMPOSITIONS WITH REDUCED CSA AGGLOMERATION

(71) Applicants: Benjamin J. Darien, Madison, WI (US); Paul B. Savage, Mapleton, UT (US)

(72) Inventors: Benjamin J. Darien, Madison, WI (US); Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 247 days.

(21) Appl. No.: 14/642,905

(22) Filed: Mar. 10, 2015

(65) Prior Publication Data

US 2015/0258121 A1   Sep. 17, 2015

Related U.S. Application Data

(60) Provisional application No. 61/952,669, filed on Mar. 13, 2014.

(51) Int. Cl.
| | |
|---|---|
| *A61K 9/16* | (2006.01) |
| *A61K 9/48* | (2006.01) |
| *A61K 31/575* | (2006.01) |
| *A61K 9/14* | (2006.01) |
| *B06B 1/00* | (2006.01) |
| *A61K 31/56* | (2006.01) |

(52) U.S. Cl.
CPC .............. *A61K 31/575* (2013.01); *A61K 9/48* (2013.01); *A61K 9/4833* (2013.01)

(58) Field of Classification Search
None
See application file for complete search history.

(56) References Cited

U.S. PATENT DOCUMENTS

| | | |
|---|---|---|
| 4,248,236 A | 2/1981 | Linder |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,972,848 A | 11/1990 | DiDomenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,721,359 A | 2/1998 | Dunn et al. |
| 6,117,332 A | 9/2000 | Hatch et al. |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,066 B2 | 10/2004 | Traeder et al. |
| 6,872,303 B2 | 3/2005 | Knapp et al. |
| 6,939,376 B2 | 9/2005 | Shulze et al. |
| 7,282,214 B2 | 10/2007 | Wilcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 9,527,883 B2 | 12/2016 | Savage et al. |
| 2002/0091278 A1 | 7/2002 | Savage et al. |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/875,953, filed Oct. 6, 2015, Savage.
U.S. Appl. No. 14/926,738, filed Oct. 29, 2015, Vazquez et al.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 2004.

(Continued)

*Primary Examiner* — Jeffrey T. Palenik
(74) *Attorney, Agent, or Firm* — Workman Nydegger

(57) ABSTRACT

Compositions and methods for preparing stabilized CSA compositions having reduced agglomeration and increased stability. The compositions have increased efficacy in killing microbes and reduced cytotoxicity to mammals. The compositions include a liquid carrier, micelles formed from an amphiphilic material, and CSA molecules encapsulated by the micelles. The CSA compositions can be formed by blending together a solvent or liquid carrier, a plurality of CSA molecules, and a micelle-forming agent and causing or allowing the micelle-forming agent to form micelles encapsulating at least a portion of the CSA molecules so that no more than 25% of the CSA molecules form agglomerates larger than 1 μm in size. The CSA compositions can be used to treat mammals, such as mammals suffering from microbial diseases or infections.

34 Claims, No Drawings

(56) References Cited

U.S. PATENT DOCUMENTS

| | | |
|---|---|---|
| 2003/0018306 A1 | 1/2003 | Bucay-Couto et al. |
| 2003/0099717 A1 | 5/2003 | Cabrera |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0134292 A1 | 6/2007 | Suokas et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0091376 A1 | 4/2011 | Savage |
| 2011/0123624 A1 | 5/2011 | Zasloff |
| 2011/0135742 A1 | 6/2011 | Kim et al. |
| 2011/0230589 A1 | 9/2011 | Maggio et al. |
| 2012/0088733 A1 | 4/2012 | Kim et al. |
| 2012/0107382 A1 | 5/2012 | Savage et al. |
| 2013/0022651 A1 | 1/2013 | Savage |
| 2013/0053507 A1 | 2/2013 | Savage |
| 2013/0234842 A1 | 9/2013 | Genberg et al. |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0315873 A1 | 10/2014 | Beus et al. |
| 2014/0336131 A1 | 11/2014 | Savage et al. |
| 2014/0363780 A1 | 12/2014 | Vazquez et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2016/0193232 A1 | 3/2016 | Beus et al. |
| 2016/0199390 A1 | 3/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |

FOREIGN PATENT DOCUMENTS

| | | |
|---|---|---|
| EP | 0341951 | 11/1989 |
| EP | 1208844 | 5/2002 |
| EP | 1219631 | 7/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 1995024415 | 9/1995 |
| WO | WO9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO 2003015757 | 2/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2009 |
| WO | WO 2009079066 | 6/2009 |
| WO | WO2009144708 | 12/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO 2013109236 | 7/2013 |

OTHER PUBLICATIONS

International Search Report for PCT Application No. PCT/US2014/034986 dated Aug. 28, 2014.
International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Zanger et al., "Structure-Activity Relationship and Drug Design", Remington's Pharmaceutical Sciences, Chapter 27, 16th Edition, 1980, pp. 420-425.
U.S. Appl. No. 13/783,007, filed Mar. 1, 2013, Savage.
U.S. Appl. No. 14/364,283, filed Jul. 29, 2014, Vazquez et al.
U.S. Appl. No. 14/602,499, filed Jan. 22, 2015, Savage.
U.S. Appl. No. 14/602,071, filed Jan. 21, 2015, Savage.
U.S. Appl. No. 14/624,200, filed Feb. 17, 2015, Savage.
U.S. Appl. No. 14/644,946, filed Mar. 11, 2015, Beus et al.
U.S. Appl. No. 14/645,040, filed Mar. 11, 2015, Savage et al.
U.S. Appl. No. 14/694,028, filed Apr. 23, 2015, Beus et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar.

(56) References Cited

OTHER PUBLICATIONS 5, 1999 (Mar. 5, 1999), pp. 1865-1868, XP004155984, ISSN: 0040-4039, DOI: 10.1016/S0040-4039(99)00075-1.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/ol0062704/suppl file/ol0062704 sl.pdf.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.

Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
P. B. Savage, et al., "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld, et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/554,957, filed Jul. 20, 2012, Office Action dated Apr. 1, 2014.
U.S. Appl. No. 13/554,957, filed Jul. 20, 2012, Notice of Allowance dated Aug. 1, 2014.
U.S. Appl. No. 13/594,608, filed Aug. 24, 2012, Office Action dated Jan. 30, 2014.
U.S. Appl. No. 13/594,612, filed Aug. 24, 2012, Office Action dated May 15, 2014.
U.S. Appl. No. 13/615,324, filed Sep. 13, 2012, Office Action dated Jan. 30, 2014.
U.S. Appl. No. 13/554,930, filed Jul. 20, 2012, Office Action dated Jul. 11, 2014.
U.S. Appl. No. 13/783,131, filed Mar. 1, 2013, Office Action dated Oct. 23, 2014.
U.S. Appl. No. 13/000,010, filed Jun. 16, 2009, Restriction Requirement dated Dec. 4, 2012.
U.S. Appl. No. 13/288,902, filed Jun. 21, 2012, Restriction Requirement dated Jun. 21, 2012.
U.S. Appl. No. 13/288,902, filed Jun. 21, 2012, Office Action dated Nov. 7, 2012.
U.S. Appl. No. 13/288,902, filed Jun. 21, 2012, Notice of Allowance dated Aug. 9, 2013.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
U.S. Appl. No. 14/056,122, filed Oct. 17, 2013, Office Action dated Sep. 3, 2014.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.

(56) References Cited

OTHER PUBLICATIONS

U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.
U.S. Appl. No. 13/841,549, filed Mar. 15, 2013, Office Action dated Apr. 23, 2015.
BASF, Pluronic® Block Copolymer NF Grades (Poloxamer NF Grades), Technical Bulletive (2004).
Bush, "Staphylococcal Infections", Merck Manuals Professional Edition, http://www.merckmanuals.com/professional/infectious-diseases/gram-positive-cocci/staphylococcal-infections, Last revised Feb. 2016.
Cipolla et al., "Inhaled antibiotics to treat lung infection", Pharm Pat Anal., Sep. 2013.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961, Jul. 2010.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824, Jun. 2002.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-676, 1954.
Papo et al., "Host peptides as new weapons in cancer treatment", CMLS Cell. Mol. Life Sci. 62 (2005), 784-790.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO—Published Dec. 20, 2007).
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.

US 10,220,045 B2

COMPOSITIONS AND METHODS FOR FORMING STABILIZED COMPOSITIONS WITH REDUCED CSA AGGLOMERATION

CROSS-REFERENCE TO RELATED APPLICATIONS

This application claims the benefit of U.S. Provisional Application No. 61/952,669, filed Mar. 13, 2014, the disclosure of which is incorporated herein in its entirety.

BACKGROUND OF THE INVENTION

1. The Field of the Invention

The present invention relates to compostions containing cationic steroidal antimicrobial (CSA) compounds with reduced CSA agglomeration and methods for making and utilizing such compositions.

2. The Relevant Technology

Cationic steroidal antimicrobial (CSA) compounds have been shown to be effective in treating diseases and infections in mammals caused by microbes. The effectiveness of CSA compounds in treating diseases and infections caused by microbes can be dependent on the concentration of the CSA compound(s) within a CSA-containing composition and/or the amount of CSA-containing composition administered.

Notwithstanding the effectiveness of CSA compounds, some CSA-containing compositions have unexpectedly shown diminished effectiveness in killing microbes, sometimes in unpredictable or unexpected ways. In some cases, CSA-containing compositions have been found to be cytotoxic to mammalian cells and therefore harmful to the mammal being treated. It can sometimes be difficult to strike the correct balance between effectiveness in killing microbes, on the one hand, and safety to the mammal being treated, on the other.

In addition, CSA-containing compositions can lose efficacy and/or form increased cytotoxicity to mammalian cells over time, sometimes in unpredictable or unexpected ways. Thus, the instability of certain CSA-containing compositions can pose difficult challenges.

Accordingly, there is a need for improved methods of preparing CSA-containing compositions that increase or maintain their efficacy in killing microbes, while, at the same time, reducing or minimizing toxicity to mammals being treated. In addition, there is a need for improved CSA-containing compositions that are able to remain stable over time.

SUMMARY

Disclosed herein are methods for preparing stabilized CSA-containing compositions that maintain or increase efficacy in killing microbes while reducing or minimizing cytotoxicity to mammalian cells. Also disclosed are CSA-containing compositions made using the disclosed methods. In some cases, CSA-containing compositions as disclosed herein are able to remain stable over longer periods of time as compared to CSA-containing compositions prepared using conventional methods. Also disclosed are methods of utilizing CSA-containing compositions to treat mammals, such as mammals suffering from disease or infection.

It has now been discovered that CSA compounds, which are generally believed to be soluble in various solvents, such as water, saline solution, or ethanol, can form agglomerates rather than remaining as a highly dispersed solute or colloidal dispersion. In some cases, CSA agglomerates form rapidly. In other cases CSA compounds can form agglomerates over time after being initially dissolved or dispersed in a solvent or carrier liquid (e.g., after days, weeks, or months). Formation of CSA agglomerates can reduce efficacy because only CSA molecules on the agglomerate surfaces are generally available to interact with and kill microbes, which can essentially remove or sequester a substantial portion of otherwise active CSA molecules from the composition. In addition, CSA agglomerates can sometimes be cytotoxic by collecting on mammalian tissue and forming localized areas of high CSA concentration rather than remaining highly dispersed throughout the CSA-containing composition.

It has now been found that negative effects caused by the previously unknown problem of CSA agglomeration and instability can be offset by forming micelles within the solvent or carrier liquid using a suitable amphiphilic compound or composition that is able to encapsulate the CSA molecules and reduce or prevent agglomeration within the composition. Examples of suitable micelle-forming amphiphilic compounds or compositions include one or more surfactants having separate hydrophobic and hydrophilic regions. Because CSA molecules are themselves amphiphilic and often behave as surfactants, the realization that utilizing a different amphiphilic compound or surfactant within the solvent or carrier liquid to form micelles that can encapsulate the CSA molecules and reduce or prevent agglomeration within the composition was not previously recognized nor readily apparent.

The preparation of CSA-containing compositions having highly dispersed CSA molecules (e.g., so that less than about 25% of the CSA molecules form agglomerates or particles 1 μm or larger in size) can be dependent on the type of solvent or liquid carrier, micelle-forming agent, and CSA compound(s) and/or the order of mixing the solvent or carrier liquid, micelle-forming agent, and CSA compound(s). In some cases, as will be explained below, the CSA compound(s) can be initially dissolved or dispersed in a suitable solvent or liquid carrier, followed by addition of one or more micelle-forming agents to form micelles that encapsulate at least a portion of the CSA molecules and prevent or reduce agglomeration. In other cases, the CSA compound(s) can be blended or dispersed with one or more micelle-forming agents to form an intermediate mixture, which is thereafter added to a suitable solvent or carrier liquid. The relative hydrophilicity and hydrophobicity of the various components may affect the order of mixing to yield a desired CSA-containing composition.

According to some embodiments, at least about 75%, 85%, 90%, or 95% of the CSA molecules within CSA-containing compositions disclosed herein are in the form of individually sequestered molecules or particles less than 1 μm in size. In some embodiments at least about 75%, 85%, 90%, or 95% of the CSA molecules are in the form of individually sequestered molecules or particles less than 500 nm in size. In some embodiments at least about 75%, 85%, 90%, or 95% of the CSA molecules are in the form of individually sequestered molecules or particles less than 100 nm in size. In some cases it may be useful to consider CSA particles less than 100 nm in size to constitute individually sequestered CSA molecules within micelles.

In some embodiments, less than about 25%, 15%, 10%, or 5% of the CSA molecules form agglomerates or particles larger than about 1 μm in size. In some embodiments, less than about 25%, 15%, 10%, or 5% of the CSA molecules form agglomerates larger than about 500 μm in size. In some embodiments, less than about 25%, 15%, 10%, or 5% of the CSA molecules form agglomerates larger than about 100 µm in size. In some cases it may be desirable to minimize or eliminate CSA agglomerates in order to maximize efficacy in killing microbes and minimize cytotoxicity to mammalian cells.

The CSA-containing compositions disclosed herein can be used in a variety of desired methods. Non-limiting examples include treating or preventing diseases or infections caused by microbes. Other examples include treating secondary effects caused by microbes, such as breaking down plaques or biofilms caused by or containing microbes, which can cause non-infectious ailments. The CSA-containing compositions can be used to treat affected hosts, such as mammals, non-limiting examples of which include bovines, cattle, horses, humans, and domestic pets.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

DETAILED DESCRIPTION

Disclosed herein are methods for reducing or eliminating formation of CSA agglomerates when preparing CSA-containing compositions, which can maintain or increase efficacy in killing microbes and reduce or minimize cytotoxicity to mammalian cells. Also disclosed are compositions made using the disclosed methods. In some cases, CSA-containing compositions can remain stable over longer periods of time as compared to CSA-containing compositions prepared using conventional methods. Also disclosed herein are methods of utilizing CSA-containing compositions in order to treat mammals, such as mammals suffering from microbial diseases or infections.

CSA compounds, generally believed to be soluble in various solvents, such as water, saline solution, or ethanol, can form agglomerates rather than a highly dispersed solute or colloidal dispersion. CSA agglomerates can unexpectedly or unpredictably form immediately or over time after being initially dissolved or dispersed in a solvent or carrier liquid. CSA agglomerates can reduce efficacy in microbes and/or can be cytotoxic to mammals being treated. The solution for reducing or preventing CSA agglomeration and instability is to form micelles within the solvent or carrier liquid. This can be done using a suitable amphiphilic compound or composition that encapsulates the CSA molecule(s) and reduces or prevents agglomeration within the CSA-composition. CSA molecules are themselves amphiphilic and can behave as surfactants. Thus, the realization that utilizing a different amphiphilic compound or surfactant within the solvent or carrier liquid to form micelles that encapsulate the CSA molecules and reduce or prevent agglomeration within the composition was not previously recognized nor readily apparent.

As used herein, a "micelle" is an aggregate of surfactant molecules dispersed in a liquid colloid. A typical micelle in an aqueous or other polar solution forms an aggregate with the hydrophilic "head" regions in contact with the surrounding solvent. The hydrophobic (e.g., single-tail) regions are sequestered in the micelle center. In some cases, this phase is caused by the packing behavior of single-tailed lipids in a bilayer. This type of micelle is known as a "normal-phase micelle" (e.g., "oil-in-water micelle"). "Inverse micelles" have the hydrophilic head groups at the micelle center, with the tails extending outwardly from the micelle surface (e.g., "water-in-oil micelle"). Micelles can be approximately spherical in shape, although other shapes, such as ellipsoids, cylinders, and bilayers, are also possible. The shape and size of a micelle are a function of the molecular geometry of its surfactant molecules and solution conditions such as surfactant concentration, temperature, pH, and ionic strength. The process of forming micelles is known as "micellisation".

Before describing exemplary compositions and methods for forming stabilized CSA compositions having reduced CSA agglomeration, as well as a more detailed description of properties, chemical characteristics, and uses, a general description will be given of non-limiting examples of CSA compounds that can be used in the disclosed compositions and methods.

I. CSA COMPOUNDS AND COMPOSITIONS

Cationic steroidal anti-microbial (CSA) compounds, sometimes referred to as "ceragenin compounds" or "ceragenins," can include synthetically produced, small molecule chemical compounds that include a sterol backbone having various charged groups (e.g., amine and cationic groups) attached to the backbone. The sterol backbone can be used to orient the amine or guanidine groups on one face, or plane, of the sterol backbone. CSA compounds are cationic and amphiphilic, based upon the functional groups attached to the backbone. They are facially amphiphilic with a hydrophobic face and a polycationic face. Without wishing to be bound to any particular theory, the anti-microbial CSA compounds described herein act as antimicrobial agents (e.g., anti-bacterials, anti-fungals, and anti-virals). It is believed, for example, that CSA compounds can act as anti-bacterials by binding to the cellular membrane of bacteria and other microbes and inserting into the cell membrane, forming a pore that allows the leakage of ions and cytoplasmic materials that are critical to the microbe's survival and leading to the death of the affected microbe. In addition, the anti-microbial CSA compounds described herein may also act to sensitize bacteria to other antibiotics. For example, at concentrations of the anti-microbial CSA compounds below the corresponding minimum bacteriostatic concentration, the CSA compound may cause bacteria to become more susceptible to other antibiotics by increasing membrane permeability. It is postulated that the charged groups are responsible for disrupting the bacterial cellular membrane and imparting anti-microbial properties.

A. Definitions

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium.

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ represent substituents that can be attached to the indicated atom. Unless otherwise specified, an R group may be substituted or unsubstituted.

The term "ring" as used herein can be heterocyclic or carbocyclic. The term "saturated" used herein refers to a fused ring having each atom in the fused ring either hydrogenated or substituted such that the valency of each atom is filled. The term "unsaturated" used herein refers to a fused ring where the valency of each atom of the fused ring may not be filled with hydrogen or other substituents. For example, adjacent carbon atoms in the fused ring can be doubly bound to each other. Unsaturation can also include deleting at least one of the following pairs and completing the valence of the ring carbon atoms at these deleted positions with a double bond; such as $R_5$ and $R_9$; $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_mO-$, $R_b(CH_2)_nO-$, $R_cC(O)O(CH_2)_pO-$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as $-CH_2-$ tethering groups, forming bonds to connect molecular fragments via their terminal carbon atoms. Examples include but are not limited to methylene ($-CH_2-$), ethylene ($-CH_2CH_2-$), propylene ($-CH_2CH_2CH_2-$), and butylene ($-CH_2CH_2CH_2CH_2-$). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys includes methoxy, ethoxy, n-propoxy, 1-methylethoxy(isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "CN" group.

A "carbonyl" or an "oxo" group refers to a C=O group.

The term "azido" as used herein refers to a —N$_3$ group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "C-carboxyalkyl" refers to a carboxy group connected, as a substituent, to an alkyl group. Examples include HO—(C=O)-alkyl, with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

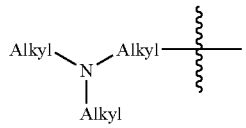

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

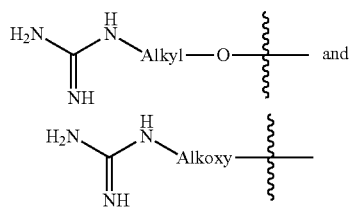

with the terms "alkyl" and "alkoxy" as defined herein.

As used herein, "guanidinoalkylcarboxy" refers to a guanidinyl group connected, as a substituent, to an alkyl group connected, as a substituent, to a carboxy group. Examples include

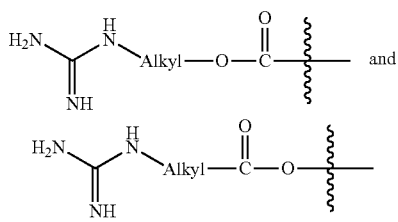

with the term "alkyl" as defined herein.

As used herein, "quaternary ammonium alkylcarboxy" refers to a quaternized amino group connected, as a substituent, to an alkyl group connected, as a substituent, to a carboxy group. Examples include

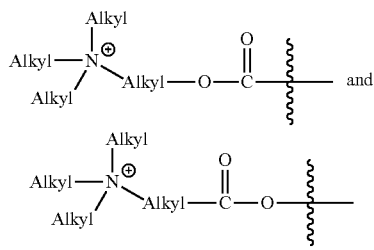

with the term "alkyl" as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA compound with a second CSA compound (which may be the same or different). An example of a linking group is (C$_1$-C$_{10}$) alkyloxy-(C$_1$-C$_{10}$) alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and aryl-alkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethyl-carbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a CSA compound differs from a compound disclosed herein only in that one or more protecting groups of the disclosed compound has been substituted with a different protecting group, that compound is within the disclosure CSA compounds may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$. A tail moiety may include the heteroatom (O or N) covalently coupled to the sterol backbone. The tail moiety may, for example, be configured to alter the hydrophobicity/hydrophilicity of the CSA compound. CSA compounds of the present disclosure having different degrees of hydrophobicity/hydrophilicity may, for example, have different rates of uptake into different target microbes. Likewise, altering the hydrophobicity/hydrophilicity of the CSA compounds described herein may affect the retention of the CSA compounds in certain media.

B. CSA Compounds

CSA Compounds useful in accordance with this disclosure are described herein, both generically and with particularity, and in U.S. Pat. Nos. 6,350,738, 6,486,148, 6,767,904, 7,598,234, 7,754,705, U.S. application Ser. Nos. 61/786,301, 13/288,892, 61/642,431, 13/554,930, 61/572,714, 13/594,608, 61/576,903, 13/594,612, 13/288,902, 61/605,639, 13/783,131, 61/605,642, 13/783,007, 61/132,361, 13/000,010, 61/534,185, 13/615,244, 61/534,194, 13/615,324, 61/534,205, 61/637,402, 13/841,549, 61/715,277, PCT/US13/37615, 61/749,800, 61/794,721, and 61/814,816, which are incorporated herein by reference. Additional compounds are generally and specifically described in relation to the methods discussed herein. The skilled artisan will recognize the compounds within the generic formulae set forth herein and understand their preparation in view of the references cited herein and the Examples.

In some embodiments, the CSA compound is a compound of Formula (I) or a pharmaceutically acceptable salt thereof:

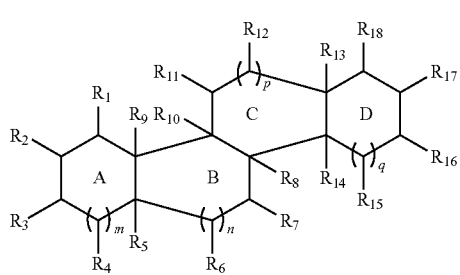

(I)

wherein:
rings A, B, C, and D are independently saturated, or are fully or partially unsaturated, provided that at least two of rings A, B, C, and D are saturated;
m, n, p, and q are independently 0 or 1;
$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, $H_2N-HC(Q_5)-C(O)-O-$, $H_2N-HC(Q_5)-C(O)-N(H)-$, a substituted or unsubstituted azidoalkyloxy, a substituted or unsubstituted cyanoalkyloxy, P.G.-HN—$HC(Q_5)-C(O)-O-$, a substituted or unsubstituted guanidinoalkyloxy, a substituted or unsubstituted quaternaryammoniumalkylcarboxy, and a substituted or unsubstituted guanidinoalkyl carboxy, where $Q_5$ is a side chain of any amino acid (including a side chain of glycine, i.e., H), and P.G. is an amino protecting group; and
$R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, $H_2N-HC(Q_5)-C(O)-O-$, $H_2N-HC(Q_5)-C(O)-N(H)-$, azidoalkyloxy, cyanoalkyloxy, P.G.-HN—$HC(Q_5)-C(O)-O-$, guanidinoalkyloxy, and guanidine-alkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a quaternaryammoniumalkylcarboxy, a substituted or unsubstituted di(alkyl) aminoalkyl, $H_2N-HC(Q_5)-C(O)-O-$, $H_2N-HC(Q_5)-C(O)-N(H)-$, azidoalkyloxy, cyanoalkyloxy, P.G.-HN—$HC(Q_5)-C(O)-O-$, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino-($C_1$-$C_{22}$) alkylamino, a substituted or unsubstituted ($C_1$-$C_{22}$) aminoalkyl, a substituted or unsubstituted aryl, a substituted or unsubstituted arylamino-($C_1$-$C_{22}$) alkyl, a substituted or unsubstituted ($C_1$-$C_{22}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkyloxy-($C_1$-$C_{22}$) alkyl, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted ($C_1$-$C_{22}$) aminoalkylcarboxamido, a substituted or unsubstituted di($C_1$-$C_{22}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{22}$) azidoalkyloxy, a substituted or unsubstituted ($C_1$-$C_{22}$) cyanoalkyloxy, P.G.-HN—HC($Q_5$)-C(O)—O—, a substituted or unsubstituted ($C_1$-$C_{22}$) guanidinoalkyloxy, a substituted or unsubstituted ($C_1$-$C_{22}$) quaternaryammoniumalkylcarboxy, and a substituted or unsubstituted ($C_1$-$C_{22}$) guanidinoalkyl carboxy, where $Q_5$ is a side chain of any amino acid (including a side chain of glycine, i.e., H), and P.G. is an amino protecting group; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{22}$) alkyl, a substituted or unsubstituted ($C_1$-$C_{22}$) hydroxyalkyl, a substituted or unsubstituted ($C_1$-$C_{22}$) alkyloxy-($C_1$-$C_{22}$) alkyl, a substituted or unsubstituted ($C_1$-$C_{22}$) aminoalkyl, a substituted or unsubstituted aryl, a substituted or unsubstituted ($C_1$-$C_{22}$) haloalkyl, a substituted or unsubstituted ($C_2$-$C_6$) alkenyl, a substituted or unsubstituted ($C_2$-$C_6$) alkynyl, oxo, a linking group attached to a second steroid, a substituted or unsubstituted ($C_1$-$C_{22}$) aminoalkyloxy, a substituted or unsubstituted ($C_1$-$C_{22}$) aminoalkylcarboxy, a substituted or unsubstituted ($C_1$-$C_{22}$) aminoalkylaminocarbonyl, a substituted or unsubstituted di($C_1$-$C_{22}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{22}$) azidoalkyloxy, a substituted or unsubstituted ($C_1$-$C_{22}$) cyanoalkyloxy, P.G.-HN—HC($Q_5$)-C(O)—O—, a substituted or unsubstituted ($C_1$-$C_{22}$) guanidinoalkyloxy, and ($C_1$-$C_{22}$) guanidinoalkylcarboxy, where $Q_5$ is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{22}$) aminoalkyl, a substituted or unsubstituted ($C_1$-$C_{22}$) aminoalkyloxy, a substituted or unsubstituted ($C_1$-$C_{22}$) alkylcarboxy-($C_1$-$C_{22}$) alkyl, a substituted or unsubstituted ($C_1$-$C_{22}$) alkylamino-($C_1$-$C_{22}$) alkylamino, a substituted or unsubstituted ($C_1$-$C_{22}$) alkylamino-($C_1$-$C_{22}$) alkylamino($C_1$-$C_{22}$) alkylamino, a substituted or unsubstituted ($C_1$-$C_{22}$) aminoalkylcarboxy, a substituted or unsubstituted arylamino ($C_1$-$C_{22}$) alkyl, a substituted or unsubstituted ($C_1$-$C_{22}$) aminoalkyloxy($C_1$-$C_{22}$) aminoalkylaminocarbonyl, a substituted or unsubstituted ($C_1$-$C_{22}$) aminoalkylaminocarbonyl, a substituted or unsubstituted ($C_1$-$C_{22}$) aminoalkylcarboxamido, a substituted or unsubstituted ($C_1$-$C_{22}$) quaternaryammoniumalkylcarboxy, a substituted or unsubstituted di($C_1$-$C_{22}$ alkyl)aminoalkyl, $H_2N$—HC($Q_5$)-C(O)—O—, $H_2N$—HC($Q_5$)-C(O)—N(H)—, a substituted or unsubstituted ($C_1$-$C_{22}$) azidoalkyloxy, a substituted or unsubstituted ($C_1$-$C_{22}$) cyanoalkyloxy, P.G.-HN—HC($Q_5$)-C(O)—O—, a substituted or unsubstituted ($C_1$-$C_{22}$) guanidinoalkyloxy, and a substituted or unsubstituted ($C_1$-$C_{22}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkyl amino-($C_1$-$C_{18}$) alkylamino, ($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl) amino alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted aryl amino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl) amino alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy.

In some embodiments, the CSA compound, or a pharmaceutically acceptable salt thereof, is selected from the compound of Formula (IA), which is a subgenus of Formula (I) in that $R_{15}$ is omitted:

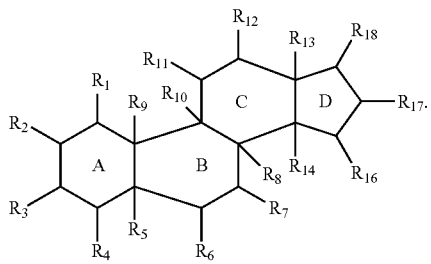

(IA)

In some embodiments, rings A, B, C, and D are independently saturated.

In some embodiments, one or more of rings A, B, C, and D are heterocyclic.

In some embodiments, rings A, B, C, and D are non-heterocyclic.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl) aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$) alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)amino alkyl; alkylaminoalkyl; alkyoxycarbonylalkyl; alkylcarboxyalkyl; and hydroxyalkyl.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy. In some embodiments, $R_{18}$ is alkylaminoalkyl. In some embodiments, $R_{18}$ is alkoxycarbonylalkyl. In some embodiments, $R_{18}$ is di(alkyl)aminoalkyl. In some embodiments, $R_{18}$ is alkylcarboxyalkyl. In some embodiments, $R_{18}$ is hydroxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, at least two, or at least three, of m, n, p, and q are 1. In some embodiments, m, n, and p are each 1 and q is 0.

In some embodiments, the CSA compound, or a pharmaceutically acceptable salt thereof, is selected from the compound of Formula (IB), which is a subgenus of Formula (IA):

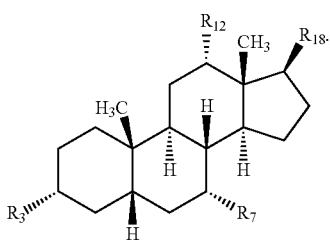

(IB)

In some embodiments, the CSA compound, or a pharmaceutically acceptable salt thereof of the compound of Formula (IB), is selected from the group consisting of:

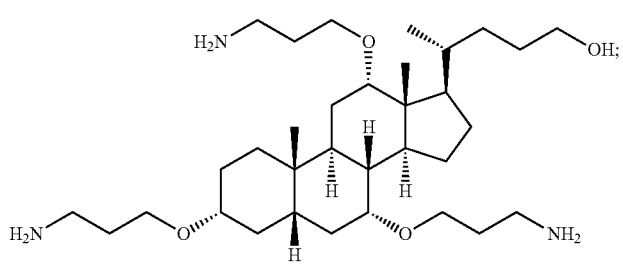

CSA-8

-continued
CSA-13
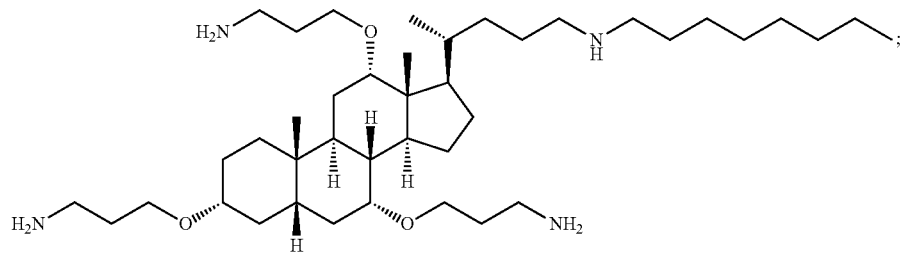
CSA-44
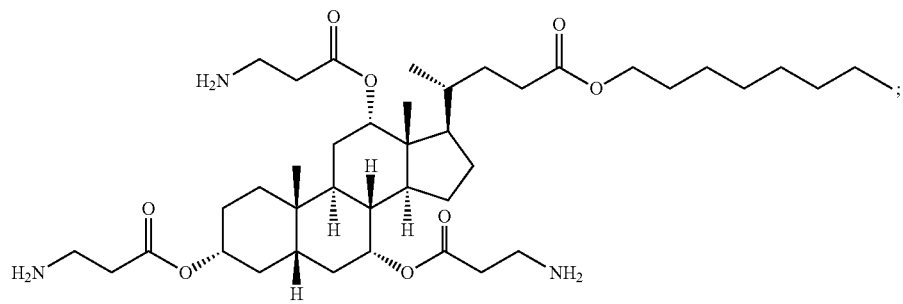
CSA-90
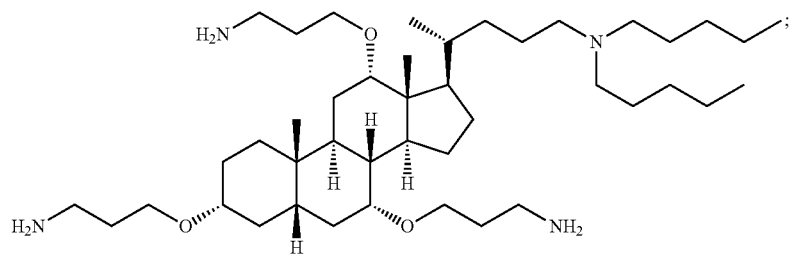
CSA-92
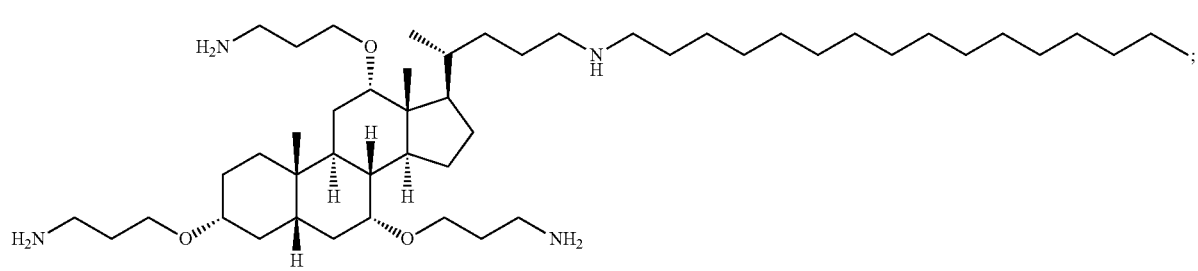
CSA-97
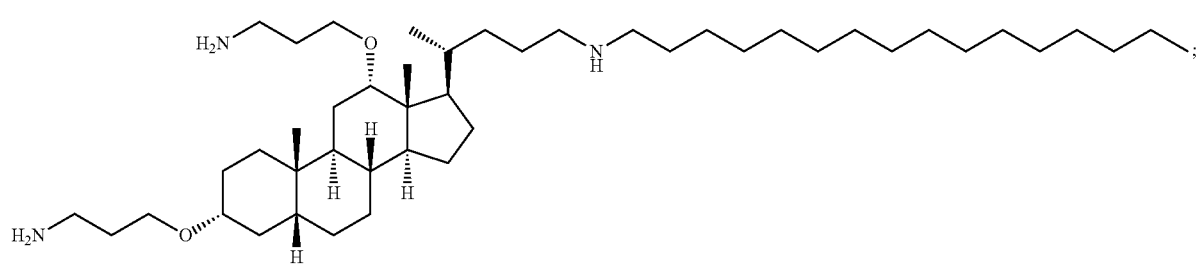

-continued
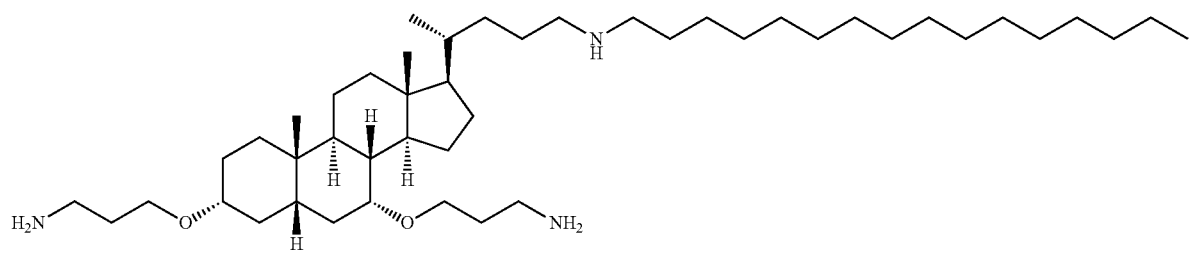
CSA-99
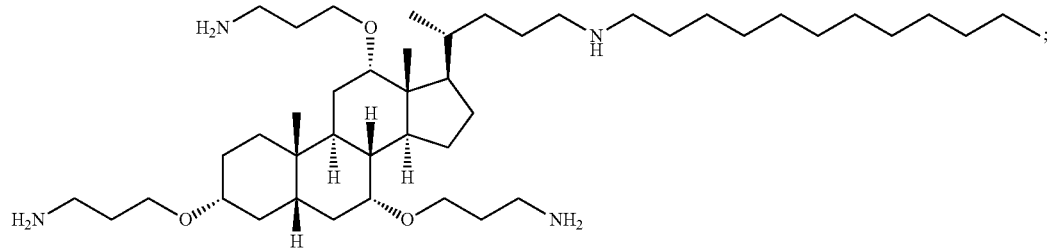
CSA-131
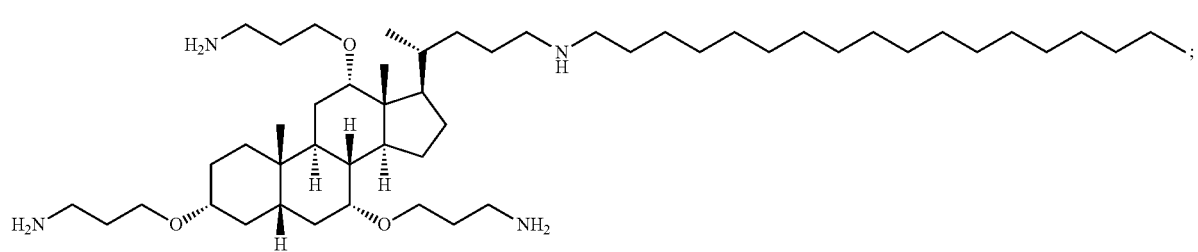
CSA-132
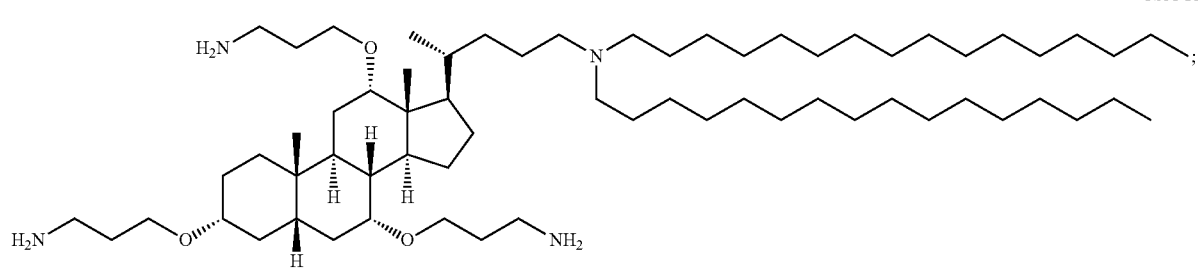
CSA-133
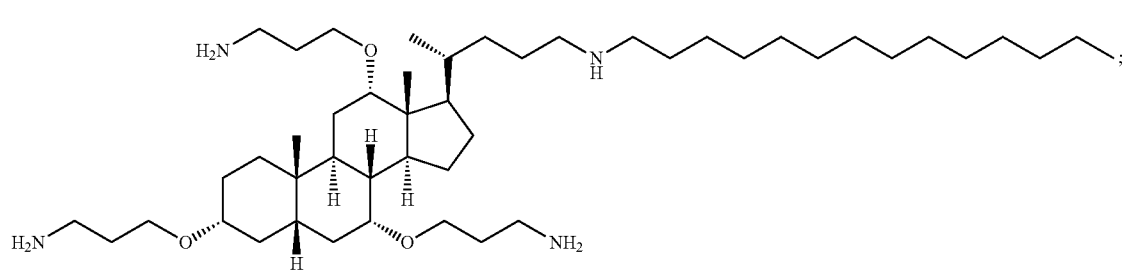
CSA-134
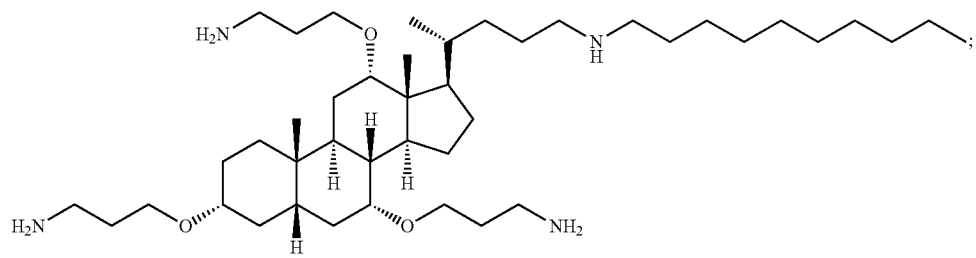
CSA-136

-continued
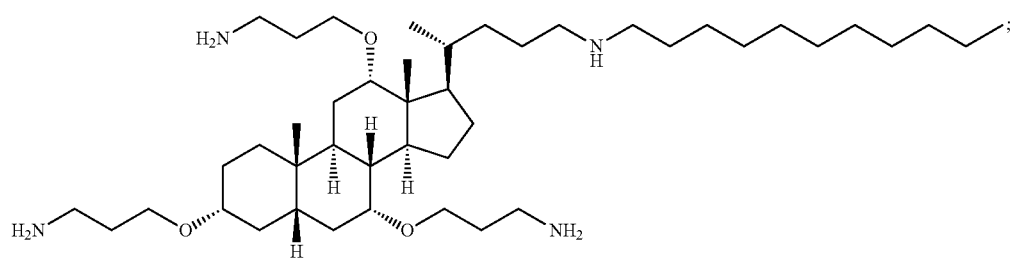
CSA-137
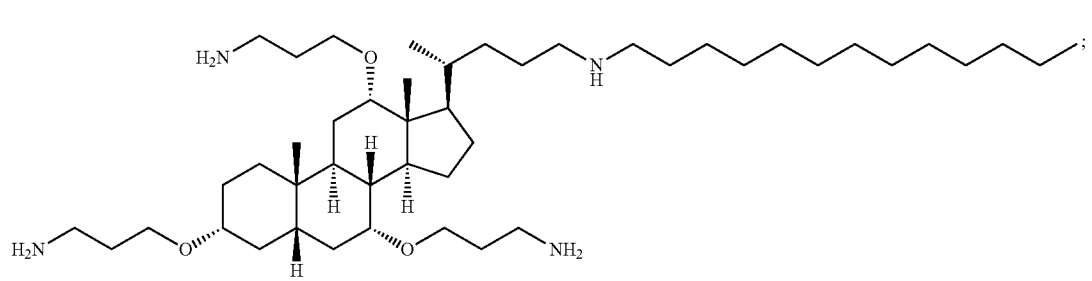
CSA-138
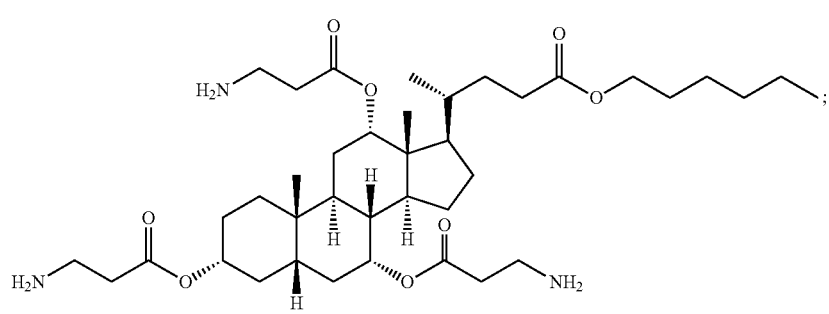
CSA-142
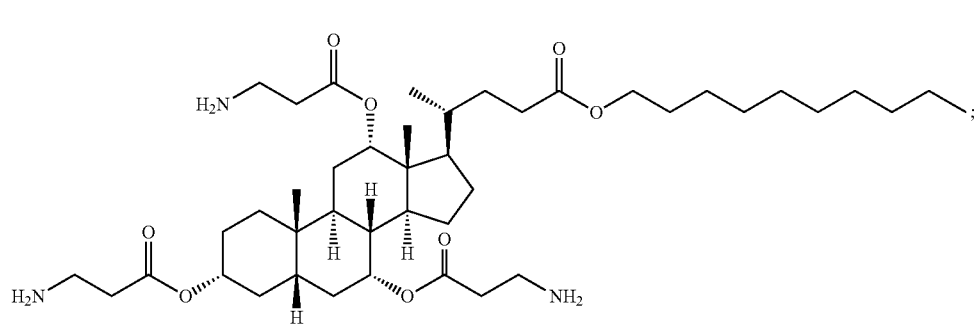
CSA-144
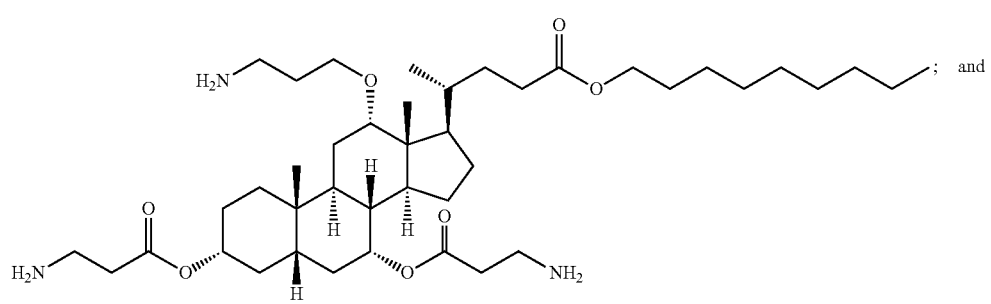
CSA-145; and

CSA-146

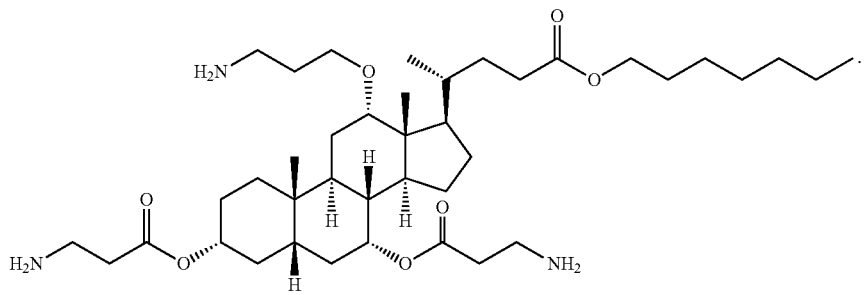

In some embodiments, the CSA compound, or a pharmaceutically acceptable salt thereof, is selected from the compound of Formula (II), which is related to, but not identical to, Formula (I), e.g., in that $R_{18}$, rather than $R_{15}$, is optional and can be omitted:

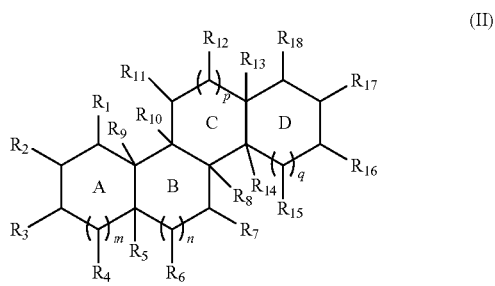

(II)

wherein rings A, B, C, and D are independently saturated, or are fully or partially unsaturated, provided that at least two of rings A, B, C, and D are saturated;

m, n, p, and q are independently 0 or 1;

each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted $(C_1\text{-}C_{10})$ alkyl, $(C_1\text{-}C_{10})$ hydroxyalkyl, $(C_1\text{-}C_{10})$ alkyloxy-$(C_1\text{-}C_{10})$ alkyl, $(C_1\text{-}C_{10})$ alkylcarboxy-$(C_1\text{-}C_{10})$ alkyl, $(C_1\text{-}C_{10})$ alkylamino-$(C_1\text{-}C_{10})$ alkyl, $(C_1\text{-}C_{10})$ alkylamino-$(C_1\text{-}C_{10})$ alkylamino, $(C_1\text{-}C_{10})$ alkylamino-$(C_1\text{-}C_{10})$ alkylamino-$(C_1\text{-}C_{10})$ alkylamino, a substituted or unsubstituted $(C_1\text{-}C_{10})$ aminoalkyl, a substituted or unsubstituted aryl, a substituted or unsubstituted arylamino-$(C_1\text{-}C_{10})$ alkyl, $(C_1\text{-}C_{10})$ haloalkyl, $C_2\text{-}C_6$ alkenyl, $C_2\text{-}C_6$ alkynyl, oxo, a linking group attached to a second steroid, a substituted or unsubstituted $(C_1\text{-}C_{10})$ aminoalkyloxy, a substituted or unsubstituted $(C_1\text{-}C_{10})$ aminoalkyloxy-$(C_1\text{-}C_{10})$ alkyl, a substituted or unsubstituted $(C_1\text{-}C_{10})$ aminoalkylcarboxy, a substituted or unsubstituted $(C_1\text{-}C_{10})$ aminoalkylaminocarbonyl, a substituted or unsubstituted $(C_1\text{-}C_{10})$ aminoalkylcarboxamido, $H_2N\text{—}HC(Q_5)\text{-}C(O)\text{—}O\text{—}$, $H_2N\text{—}HC(Q_5)\text{-}C(O)\text{—}N(H)\text{—}$, $(C_1\text{-}C_{10})$ azidoalkyloxy, $(C_1\text{-}C_{10})$ cyanoalkyloxy, P.G.-HN—HC$(Q_5)$-C(O)—O—, $(C_1\text{-}C_{10})$ guanidinoalkyloxy, $(C_1\text{-}C_{10})$ quaternary ammonium alkylcarboxy, and $(C_1\text{-}C_{10})$ guanidinoalkyl carboxy, where $Q_5$ is a side chain of any amino acid (including a side chain of glycine, i.e., H), P.G. is an amino protecting group; and each of $R_5$, $R_8$, $R_9$, $R_{10}$, $R_{13}$, and $R_{14}$ may be independently deleted when one of fused rings A, B, C, or D is unsaturated so as to complete the valency of the carbon atom at that site, or selected from the group consisting of hydrogen, hydroxyl, a substituted or unsubstituted $(C_1\text{-}C_{10})$ alkyl, $(C_1\text{-}C_{10})$ hydroxyalkyl, $(C_1\text{-}C_{10})$ alkyloxy-$(C_1\text{-}C_{10})$ alkyl, a substituted or unsubstituted $(C_1\text{-}C_{10})$ aminoalkyl, a substituted or unsubstituted aryl, $(C_1\text{-}C_{10})$ haloalkyl, $C_2\text{-}C_6$ alkenyl, $C_2\text{-}C_6$ alkynyl, oxo, a linking group attached to a second steroid, a substituted or unsubstituted $(C_1\text{-}C_{10})$ aminoalkyloxy, a substituted or unsubstituted $(C_1\text{-}C_{10})$ aminoalkylcarboxy, a substituted or unsubstituted $(C_1\text{-}C_{10})$ aminoalkylaminocarbonyl, $H_2N\text{—}HC(Q_5)\text{-}C(O)\text{—}O\text{—}$, $H_2N\text{—}HC(Q_5)\text{-}C(O)\text{—}N(H)\text{—}$, $(C_1\text{-}C_{10})$ azidoalkyloxy, $(C_1\text{-}C_{10})$ cyanoalkyloxy, P.G.-HN—HC$(Q_5)$-C(O)—O—, $(C_1\text{-}C_{10})$ guanidinoalkyloxy, and $(C_1\text{-}C_{10})$ guanidinoalkylcarboxy, where $Q_5$ is a side chain of any amino acid, P.G. is an amino protecting group, provided that at least two or three of $R_{1\text{-}4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1\text{-}C_{10})$ aminoalkyl, a substituted or unsubstituted $(C_1\text{-}C_{10})$ aminoalkyloxy, $(C_1\text{-}C_{10})$ alkylcarboxy-$(C_1\text{-}C_{10})$ alkyl, $(C_1\text{-}C_{10})$ alkylamino-$(C_1\text{-}C_{10})$ alkylamino, $(C_1\text{-}C_{10})$ alkylamino-$(C_1\text{-}C_{10})$ alkylamino-$(C_1\text{-}C_{10})$ alkylamino, a substituted or unsubstituted $(C_1\text{-}C_{10})$ aminoalkylcarboxy, a substituted or unsubstituted arylamino($C_1\text{-}C_{10}$) alkyl, a substituted or unsubstituted $(C_1\text{-}C_{10})$ aminoalkyloxy-$(C_1\text{-}C_{10})$ aminoalkylaminocarbonyl, a substituted or unsubstituted $(C_1\text{-}C_{10})$ aminoalkylaminocarbonyl, a substituted or unsubstituted $(C_1\text{-}C_5)$ aminoalkylcarboxyamido, a $(C_1\text{-}C_{10})$ quaternary ammonium alkylcarboxy, $H_2N\text{—}HC(Q_5)\text{-}C(O)\text{—}O\text{—}$, $H_2N\text{—}HC(Q_5)\text{-}C(O)\text{—}N(H)\text{—}$, $(C_1\text{-}C_{10})$ azidoalkyloxy, $(C_1\text{-}C_{10})$ cyanoalkyloxy, P.G.-HN—HC$(Q_5)$-C(O)—O—, $(C_1\text{-}C_{10})$ guanidine-alkyloxy, and a $(C_1\text{-}C_{10})$ guanidinoalkylcarboxy.

In Formula (II), at least two or three of $R_3$, $R_7$, or $R_{12}$ may independently include a cationic moiety attached to the Formula (II) structure via a hydrolysable linkage. Optionally, a tail moiety may be attached to Formula (II) at $R_{17}$. The tail moiety may be charged, uncharged, polar, nonpolar, hydrophobic, amphipathic, and the like. Although not required, at least two or three of m, n, p. and q can be 1. In a preferred embodiment, m, n, and p=1 and q=0.

In some embodiments, the compound of Formula (II) or pharmaceutically acceptable salt can be represented by Formula (IIA), which is a subgenus of Formula (II) in that $R_{18}$ is omitted:

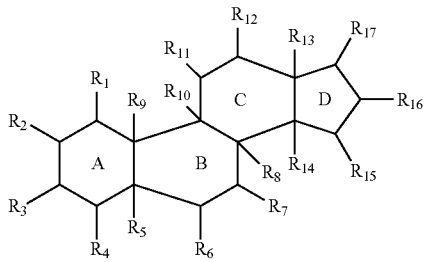

(IIA)

wherein fused rings A, B, C, and D are independently saturated or fully or partially unsaturated;

each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, $C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, ($C_1$-$C_{10}$) quaternary ammonium alkylcarboxy, and ($C_1$-$C_{10}$) guanidinoalkyl carboxy, where $Q_5$ is a side chain of any amino acid (including the side chain of glycine, i.e., H), PG. is an amino protecting group;

$R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, $C_1$-$C_{10}$ haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidine-alkyloxy, and ($C_1$-$C_{10}$) guanidinoalkylcarboxy, where $Q_5$ is a side chain of any amino acid, PG. is an amino protecting group; and at least two of $R_1$ through $R_{14}$ are independently selected from the group consisting of a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkylcarboxy, a substituted or unsubstituted arylamino($C_1$-$C_{10}$) alkyl, a substituted or unsubstituted ($C_1$-$C_{10}$) amino alkyloxy-($C_1$-$C_{10}$) alkyl, a substituted or unsubstituted ($C_1$-$C_{10}$) aminoalkylaminocarbonyl, ($C_1$-$C_{10}$) quaternary ammonium alkylcarboxy, $H_2N$—HC($Q_5$)C(O)—O—, $H_2N$—HC($Q_5$)-C(O)—N(H)—, ($C_1$-$C_{10}$) azidoalkyloxy, ($C_1$-$C_{10}$) cyanoalkyloxy, PG.-HN—HC($Q_5$)-C(O)—O—, ($C_1$-$C_{10}$) guanidinoalkyloxy, and ($C_1$-$C_{10}$) guanidinoalkylcarboxy.

In some embodiments, compounds comprise a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group.

C. Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. Additional examples of pharmaceutically acceptable salts include sulfuric acid addition salts and sulfonic acid addition salts. 1,5-naphthalenedisulfonic acid is a particularly useful sulfonic acid addition salt.

D. Pharmaceutical Compositions

While it is possible for the compounds described herein to be administered alone, it may be desirable to formulate compounds as pharmaceutical compositions. As such, in yet another aspect, pharmaceutical compositions useful in the methods and uses of the disclosed embodiments are provided. More particularly, the pharmaceutical compositions described herein may be useful, inter alia, for treating or preventing a bone disease and/or a broken bone. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. A mammal includes any mammal, such as by way of non-limiting example, cattle, pigs, sheep, goats, horses, camels, buffalo, cats, dogs, rats, mice, humans, and primates.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA compound), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Pharmaceutical compositions may be formulated as suspensions comprising a compound of the embodiments in admixture with at least one pharmaceutically acceptable excipient suitable for the manufacture of a suspension. In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol (propylene glycol).

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In applications where DMSO is not prohibited, the active may first be dissolved in DMSO and then diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprises a therapeutically or prophylactically effective amount of a compound described herein, together with at least one pharmaceutically acceptable excipient selected from the group consisting of—medium chain fatty acids or propylene glycol esters thereof (e.g., propylene glycol esters of edible fatty acids such as caprylic and capric fatty acids) and pharmaceutically acceptable surfactants such as Polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition contains a total amount of the active ingredient(s) sufficient to achieve an intended therapeutic effect.

II. STABILIZED COMPOSITIONS WITH REDUCED AGGLOMERATION

CSA compounds are generally believed to be soluble in various solvents, such as water, saline solution, or ethanol. However, it has now been found that CSA compounds can form agglomerates rather than a highly dispersed solute. CSA agglomerates can form immediately or over time after being initially dissolved or dispersed in a solvent or carrier liquid. The solution to this previously unknown problem is to form micelles within the solvent or carrier liquid using a suitable amphiphilic compound or composition so as to encapsulate the CSA molecules and reduce or prevent agglomeration within the composition.

Examples of suitable amphiphilic compounds or compositions include one or more surfactants having separate hydrophobic and hydrophilic regions. Because CSA molecules are themselves amphiphilic and can behave as surfactants, the realization that utilizing a different amphiphilic compound or surfactant within the solvent or carrier liquid to form micelles that encapsulate the CSA molecules and reduce or prevent agglomeration within the composition was not readily apparent.

As illustrated by the Examples set forth below, the components, amounts, order of mixing, and/or other conditions can affect the degree of short-term dispersion and/or long-term stability of the CSA compositions or dispersions disclosed herein. One exemplary method for forming stabilized CSA compositions with reduced agglomerate includes the steps of: (1) initially dissolving or dispersing one or more CSA compounds in an appropriate solvent, such as ethanol, which may not by itself be the desired carrier liquid in the final composition, to form a stock CSA composition; (2) separately preparing a micelle-forming composition by mixing one or more micelle-forming agents with an appropriate liquid carrier or solvent to form a micelle-forming composition that contains or will later contain micelles suitable for encapsulating CSA compounds; (3) mixing the stock CSA composition with the micelle-forming composition; (4) causing or allowing micelles to encapsulate and stabilize at least a portion of the CSA compounds in the composition; (5) sonicating one or more of the compositions obtained in steps (1) to (4); and (6) optionally adding a solvent, other liquid carrier component, additional micelle-forming agent, additional CSA compound, or other component to the composition(s) obtained in any of steps (1) to (4).

An alternative method for forming stabilized CSA compositions with reduced agglomerate includes the steps of: (1) initially mixing one or more CSA compounds with one or more micelle-forming agents to form an intermediate stock composition; (2) mixing the intermediate stock composition with an appropriate liquid carrier or solvent; (3) causing or allowing micelles to encapsulate and stabilize at least a portion of the CSA compounds in the composition; (4) sonicating one or more of the compositions obtained in steps (1) to (3); and (5) optionally adding a solvent, other liquid carrier component, additional micelle-forming agent, additional CSA compound, or other component to the composition(s) obtained in any of steps (1) to (3).

Yet another alternative method for forming stabilized CSA compositions with reduced agglomerate includes the steps of: (1) initially mixing one or more CSA compounds with a first micelle-forming agent to form a CSA stock composition; (2) separately mixing a second micelle-forming agent with an appropriate liquid carrier or solvent to form a micelle-forming stock composition; (3) mixing the CSA stock composition with the micelle-forming stock composition; (4) causing or allowing micelles to encapsulate and stabilize at least a portion of the CSA compounds in the composition; (5) sonicating one or more of the compositions obtained in steps (1) to (4); and (6) optionally adding a solvent, other liquid carrier component, additional micelle-forming agent, additional CSA compound, or other component to the composition(s) obtained in any of steps (1) to (3).

Other methods of forming stabilized CSA compositions will become apparent in view of the totality of the disclosure. The particular method of preparing such compositions, including materials selection, order of mixing, and other conditions can be selected depending on the composition being formed and can be optimized using the concepts and examples disclosed herein.

A. Micelle-Forming Agents

Examples of micelle-forming agents include a wide variety of amphillilic materials that are able to become appropriately aligned when mixed with an appropriate liquid carrier so as to form micelles. It is especially desirable for the micelles so formed to form micelle centers that have an affinity for and are therefore capable of encapsulating one or a small number of CSA molecules in order to reduce or prevent agglomeration and yield stabilized compositions. Some materials that form micelles when mixed with one type of liquid carrier may not form micelles in another liquid carrier or outside of certain concentration ranges. Nevertheless, so long as a material is able to form micelles in at least one type of liquid carrier and/or at certain concentrations, it will be considered to be a "micelle-forming agent".

Examples of micelle-forming agents include, but are not limited to, modified celluloses, modified surfactants, modified non-oxidizing vehicles, and organic acids. More specific examples include modified nonionic hydroxyethyl cellulose, natural polyoxyethylene sorbitol ester, hydroxyethyl cellulose, 2-hydroxyethyl cellulose with molecular weights between 90,000 and 750,000 with a viscosity between 50-500 cps in solutions between 1% and 5% water at temperatures between 20° C. and 25° C., modified aqueous solutions of polysorbate nonionic surfactants, polyoxyethylene sorbitan mono-, di-, and tri-($C_{12}$-$C_{18}$)-alkanoates, poloxamers, which are nonionic triblock copolymers composed of a central hydrophobic chain of polyoxypropylene (poly(propylene oxide)) flanked by two hydrophilic chains of polyoxyethylene (poly(ethylene oxide)), examples of which are sold under the tradename PLURONIC, a non-limiting example of which includes PLURONIC F-127, polyoxyethylene(20) sorbitan trioleate sold under the tradename TWEEN™ 85, polyoxyethylene(20) sorbitan monooleate sold under the tradename TWEEN™ 80, polyoxy-ethylene(20) sorbitan monostearate sold under the tradename TWEEN™ 60, polyoxyethyl-ene (20) sorbitan monopalmitate sold under the tradename TWEEN™ 40, and polyoxyethyl-ene(20) sorbitan monolaurate sold under the tradename TWEEN™ 20, hydroxymethyl cellulose, ethyl cellulose, methyl cellulose (e.g., Methocel), hydroxypropyl cellulose, carboxymethyl cellulose, emulsifying waxes, alkyl triammonium methosulfate, ceteraryloctanoate, polyols, and polyalkylene glycols having alkylene moieties containing about 2-3 carbon atoms.

B. Liquids and Solvents

In general, any appropriate liquid carrier or solvent may be used to manufacture stable CSA compositions. Determining factors for liquid carrier or solvent selection include the particular CSA compound(s) being used, the CSA concentration, the mode of delivery, and the amount of delivery. One important consideration is to select a carrier liquid or solvent so that the composition is not toxic or unduly harmful to the mammal being treated. Some liquids or solvents may be toxic at higher concentrations and safe or less toxic at lower concentrations.

Exemplary liquid carriers or solvents include, but are not limited to, water (e.g., distilled water), aqueous solutions, sugar solutions, saline solutions, lactated Ringer's Solution, alcohol (e.g., ethanol), aqueous alcohol solutions, aqueous acid solutions (e.g., organic and/or inorganic acid solutions, such as acetic acid, lactic acid, and the like), aqueous acid salt solutions, glycerine, propylene glycol, 1,3-propanediol, polypropylene glycol, and polyethylene glycol.

C. Characteristics of CSA Compositions with Reduced Agglomeration

According to some embodiments the CSA-containing compositions having reduced short-term and/or long-term agglomeration and increased stability will include some amount of CSA compounds encapsulated by micelles. In some cases, at least a substantial portion of the CSA compounds can be individually encapsulated within corresponding individual micelles. In addition or alternatively at least a substantial portion of CSA molecules can form small agglomerates having a relatively small number of CSA molecules that are encapsulated within corresponding micelles.

According to one methodoloty for determining how well the CSA compounds are dispersed, the particle size of the CSA compounds rather than the number of CSA molecules within agglomerates and/or which are encapsulated within a given micelle will be the metric. Particle size can in many cases be more easily measured than the number of CSA molecules within agglomerates and is, in any event, an appropriate approximation of the level of agglomeration, or the absence of agglomeration, of CSA molecules within the CSA composition.

In some cases it may be desirable to minimize or eliminate CSA agglomerates in order to maximize efficacy in killing microbes and minimize cytotoxicity to mammalian cells.

The particle size distribution of the CSA compounds can be determined using any known particle size analyzer or analysis method. Examples include sieving, optical or electron microscope analysis, laser diffraction, x-ray diffraction, sedimentation, elutriation, microscope counting, Coulter counter, and Dynamic Light Scattering.

According to some embodiments, at least about 75%, of the CSA molecules within CSA-containing compositions are in the form of individually sequestered molecules and/or particles less than about 1 µm in size, preferably at least about 80%, more preferably at least about 85%, even more preferably at least about 90%, and most preferably at least about or 95% of the CSA molecules within CSA-containing compositions are in the form of individually sequestered molecules and/or particles less than about 1 µm in size.

In other embodiments, at least about 75%, of the CSA molecules within CSA-containing compositions are in the form of individually sequestered molecules and/or particles less than about 500 nm in size, preferably at least about 80%, more preferably at least about 85%, even more preferably at least about 90%, and most preferably at least about or 95% of the CSA molecules within CSA-containing compositions are in the form of individually sequestered molecules and/or particles less than about 500 nm in size.

In yet other embodiments, at least about 75%, of the CSA molecules within CSA-containing compositions are in the form of individually sequestered molecules and/or particles less than about 250 nm in size, preferably at least about 80%, more preferably at least about 85%, even more preferably at least about 90%, and most preferably at least about or 95% of the CSA molecules within CSA-containing compositions are in the form of individually sequestered molecules and/or particles less than about 250 nm in size.

In still other embodiments, at least about 75%, of the CSA molecules within CSA-containing compositions are in the form of individually sequestered molecules and/or particles less than about 100 nm in size, preferably at least about 80%, more preferably at least about 85%, even more preferably at least about 90%, and most preferably at least about or 95% of the CSA molecules within CSA-containing compositions are in the form of individually sequestered molecules and/or particles less than about 100 nm in size.

In some embodiments, less than about 25% of the CSA molecules form agglomerates larger than about 1 µm in size, preferably less than about 20%, more preferably less than about 15%, even more preferably less than about 10%, and most preferably less than about 5% of the CSA molecules form agglomerates larger than about 1 µm in size.

In other embodiments, less than about 25% of the CSA molecules form agglomerates larger than about 500 nm in size, preferably less than about 20%, more preferably less than about 15%, even more preferably less than about 10%, and most preferably less than about 5% of the CSA molecules form agglomerates larger than about 500 nm in size.

In yet other embodiments, less than about 25% of the CSA molecules form agglomerates larger than about 250 nm in size, preferably less than about 20%, more preferably less than about 15%, even more preferably less than about 10%, and most preferably less than about 5% of the CSA molecules form agglomerates larger than about 250 nm in size.

In still other embodiments, less than about 25% of the CSA molecules form agglomerates larger than about 100 nm in size, preferably less than about 20%, more preferably less than about 15%, even more preferably less than about 10%, and most preferably less than about 5% of the CSA molecules form agglomerates larger than about 100 nm in size.

In some embodiments, the long-term stability of CSA compositions can be measured by the amount of percentage of particles within a desired size range. For example, stable CSA compositions can have a stability such that at least about 75% of the CSA compounds remain as individually sequestered molecules and/or are within a selected particle size range for a time period of at least 1, 2, 3, 4, 5 or 6 months, preferably at least about 80%, more preferably at least about 85%, even more preferably at least about 90%, and most preferably at least about 95% of the CSA compounds remain as individually sequestered molecules and/or are within a selected particle size range for a time period of at least 1, 2, 3, 4, 5 or 6 months.

III. METHODS OF USE

The CSA compositions disclosed herein can be used for any desired purpose, including anti-pathogenic treatments, such as antimicrobial, anti-viral, and/or antifungal treatments. The concentration and/or amount of CSA compound(s) delivered can depend on the particular treatment and can be optimized through routine testing.

Examples of possible uses include treating or preventing infections or disease caused by microbes. Other examples include treating secondary effects caused by microbes, such as breaking down plaques or biofilms caused by or containing microbes, which can cause non-infectious ailments. The CSA-containing compositions can be used to treat affected hosts, such as mammals, non-limiting examples of which include bovines, cattle, horses, humans, and domestic pets.

According to some exemplary methods of use, stabilized CSA compositions can be used to treat mastitis, infertility caused by microbial plaque or film located in a uterus (e.g., metritis or endometritis), disinfecting wounds, promoting wound healing, and treating burns and other inflammation. In the case of mastitis, the stabilized CSA composition kills bacteria that causes inflammation of the mammary gland and/or removes plaque that can block ducts involved in lactation. In the case of treating infertility resulting from metritis or endometritis, the stabilized CSA composition hastens uterine epithelial cell healing (due to its epitheliotrophic activity), and modulates the inflammation (due to enhanced innate immune response).

By way of example, some embodiments are methods of preventing or inhibiting mastitis in a subject in need of treatment for mastitis, where the mammal has a clinical case or a subclinical case of mastitis. The method includes identifying a subject in need of treatment or prevention of mastitis and administering at least one CSA formulation. Examples of subjects in need of prevention of mastitis are dairy cows that are lactating and have clinical mastitis. A dairy cow with clinical mastitis may be separated from a herd for treatment or may be treated while producing milk for consumption. Since the CSA formulations are effective without an anti-biotic, the treatments described herein can be used without contaminating the milk with anti-biotic. This allows the dairy cow to be treated without the loss of production associated with many other forms of mastitis treatment.

In an example, the dairy cow can be lactating and have a somatic cell count (SCC) less than or equal to 500,000 cells/mL at the time of administering the CSA formulation. Alternatively, the dairy cow can be lactating and have a somatic cell count (SCC) greater than 500,000 cells/mL at the time of administering the CSA formulation. In some cases, the dairy cow can be taken out of production during the administration of the CSA formulation, e.g., for a period of time of about 3 days or less, 2 days or less, or 1 day or less.

The CSA compositions can also be administered to lactating subclinical animals (i.e., mammals with below clinical numbers of somatic cells). In this embodiment, the CSA composition is used to prevent clinical mastitis. Because the CSA compounds can be used without affecting milk production, while not contaminating the milk with antibiotic, the CSA compositions are useful for preventative treatments of mastitis.

In some embodiments, the CSA compositions can be administered to non-lactating or "dry" subjects. The mammary organ of a mammal can become infected with mastitis causing bacteria prior to lactating. Administering the CSA compound to the subject before lactation commences can prevent mastitis at the onset of lactation.

The compositions disclosed herein can be administered intra-mammary in any way suitable for delivering a therapeutic amount of the compound. The compounds can be administered by injection, orally, topically or by other suitable method. In some embodiments the CSA formulation is injected intra-mammary. For example, injections can be carried out using a syringe. The injections may be performed through the teat of the mammary organ. For treating clinical mastitis, injections can be beneficial because of the high dosage that can be applied locally to the affected area. In some embodiments, the CSA formulation can be administered as a teat dip in which the teat is coated with the CSA formulation. Teat dip is particularly suited for preventative measures and can be used on clinical or subclinical animals and/or lactating or non-lactating animals.

One of ordinary skill in the art to which these exemplary embodiments belong will understand that the compositions may be administered in numerous ways. For example, typical administration is by injecting a CSA formulation directly into the mammary organ of the subject (e.g., the udder of a cow). However, other routes of administration can also be performed so long as the compound is delivered intra-mammary in the effective concentrations for treating the mastitis. In some exemplary embodiments, administration may be intravenous, oral, or topical.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the targeted area; non-encapsulated compositions can also be provided for an immediate effect.

CSA compositions can be administered at any desired frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects, the therapeutic indication, and the mode of administration. Alternatively dosages may be based and calculated upon the surface area of the patient, as understood by those of skill in the art. Although the exact dosage will be determined on a drug-by-drug basis, some generalizations regarding the dosage can be made. In some embodiments, the dosage regimen for local or systemic delivery (based on the weight of the subject) may be about 1 µg/g, 5 µg/g, 10 µg/g, 50 µg/g, 100 µg/g, 200 µg/g, 500 µg/g, 750 µg/g, 1000 µg/g, or less than any of the aforementioned numbers, or a range bounded by any two of the aforementioned numbers. In some embodiments, between about 0.001 mg to about 3000 mg of the active ingredient is delivered is administered locally or systemically. In some embodiments, about 5-15 mg of active ingredient is administered locally or systemically. In other embodiments, about 0.001 mg, 0.01 mg, 0.1 mg, 1 mg, 5 mg, 10 mg, 15 mg, 25 mg, 50 mg, 100 mg, 500 mg, 1000 mg, or less than any of the aforementioned numbers, or a range bounded by any two of the aforementioned numbers is administered locally or systemically. The dosage may be a single one or a series of two or more given in the course of one or more days, as is needed by the subject. In some embodiments, the compounds will be administered for a period of continuous therapy, for example for a week or more, or for months or years.

In instances where animal and/or human dosages for different compounds having been established for at least some condition, those same dosages may be used, or dosages that are between about 0.1% and 500%, more preferably between about 25% and 250% of the established animal and/or human dosage. For examples, dosages for INFUSE® BMP-2 and/or OP-1 BMP-7 are known and can be used to infer dosages for use in the disclosed embodiments. Where no animal and/or human dosage is established, as will be the case for newly-discovered pharmaceutical compositions, a suitable animal and/or human dosage can be inferred from ED50 or ID50 values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Some embodiments include kits comprising CSA compositions and instructions on disclosed methods. In some embodiments, kits include compounds (e.g., CSA), combination compositions and pharmaceutical compositions/formulations thereof, packaged into a suitable packaging material. In one embodiment, a kit includes packaging material, a CSA, and instructions. In various aspects, the instructions are for administering the CSA to: provide a subject with treatment or protection against mastitis; treat a subject for mastitis; decrease susceptibility of a subject to a pathogenesis; or decrease or prevent an adverse side effect caused by a pathogenesis.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with growth factors, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

IV. EXAMPLES

The Examples set forth herein are derived from data of a series of tests of compositions made using CSAs, liquid carriers, solvents, and other components, wherein different variables were examined in order to identify CSA compositions having reduced agglomeration when initially made and/or over a given time period. Raw data from such tests are set forth in the Appendix attached to this Provisional Application. The Appendix includes data in various documents and tables, including raw data and summaries of the raw data. One table sets forth raw data for CSA composition samples 1 through 67. Another table highlights comparative data for a subset of samples 1 through 67. Other documents show test data for individual samples, including graphical data of particle size.

The examples set forth below begin with preparatory examples of stock (or intermediate) compositions used to make the test compositions, followed by test compositions made from the stock compositions and that were evaluated for efficacy in reducing CSA agglomeration.

By way of example and not limitation, the CSA compound referenced in the following examples was CSA-44, which has the following chemical structure:

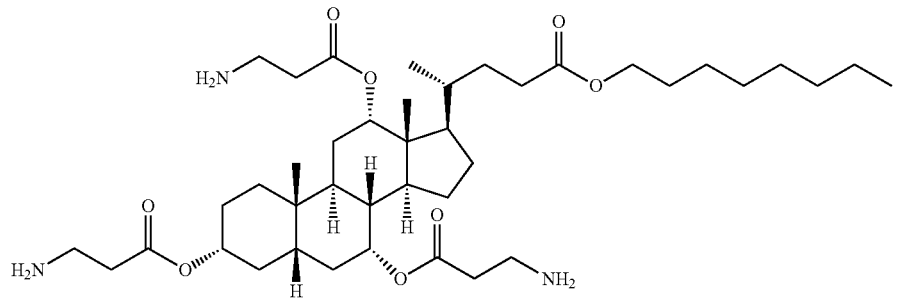

It will be appreciated that the examples set forth herein can be used in reducing agglomeration of other CSA compounds disclosed herein since all CSA compounds have similar chemical and structural characteristics. To the extent that one CSA differs from another, the principles disclosed herein will permit one of skill in the art to modify and the examples herein in order to reduce agglomeration of any, if not all, CSA compounds disclosed herein.

Preparatory Example 1

Preparation of 10% Pluronic F-127 Stock Solution

A stock aqueous solution of 10% Pluronic F-127 was made by slowly adding 10 mg of Pluronic F-127 over a period of 2-3 minutes to 90 ml of cold water (5-10° C.) in a 250 ml beaker while mixing with a magnetic stir bar. Thereafter, the mixture was permitted to form a gel, either by leaving the beaker it in a quiescent state at 4° for at least 12 hours or slowly mixed while cooling the beaker in an ice bath for about 4 hours. After mixing and warming to room temperature a gel formed. The stock solution was stored for later use at 20-23° C. in a capped container and protected from light.

Alternatively, a stock aqueous solution of 10% Pluronic F-127 was made by sprinkling 10 mg of Pluronic F-127 over a period of approximately 10 minutes to 90 ml of double distilled water in a beaker while mixing with a magnetic stir bar for at least 30 minutes. The stock solution was stored for later use at 20-23° C. in a capped container and protected from light and moisture.

Preparatory Example 2

Preparation of 20% Tween 20 Stock Solution w/v

A stock aqueous solution of 20% Tween 20 was made placing 20 g of Tween 20 into a glass beaker, adding 80 ml of double distilled water to the beaker containing the Tween 20, and mixing with a magnetic stirrer for 15 minutes. While continuing the mix the solution, approximately 20 ml of the solution was removed using a plastic syringe, filtered using a 0.22 μm filter, and stored in a capped container at room temperature.

Preparatory Example 3

Preparation of 2% hydroxyethyl cellulose Stock Solution

A stock aqueous solution of 2% hydroxyethyl cellulose (HEC, MW=90,000) was made placing 490 nml of double distilled water into a 600 ml glass beaker with a magnetic stir bar and, while stirring the water, sprinkling 10 g of hydroxyethyl into the beaker over a period of 5 minutes to prevent formation of chunks. The mixture was heated to 40° C. with continued stirring for 2 hours, yielding a solution that was not 100% clear. The mixture was then allowed to cool to room temperature with continued stirring, which took about 45 minutes. The 2% HEC solution and stir bar were transferred into a glass jar, which was capped and placed into a refrigerator at 4° C. overnight. Thereafter the stock solution was stirred for 15 minutes, following by sonication in a tub sonicator for 15 minutes. At least 20 ml of the 2% HEC solution was ultracentrifuged at 18,000×g for 1 hour at 10° C. The supernatant fluid was removed without disturbing the pellet, sonicated for 15 minutes, filtered using a 0.45 μm syringe filter, and stored in a capped container at room temperature.

Preparatory Example 4

Preparation of 250 mg/ml CSA-44 in Ethanol Stock Solution

The pH of 100% ethanol was adjusted to 4.5 using 85% lactic acid and then the ethanol was filtered using a 0.22 μm syringe filter. 1 g CSA-44 was added to a 50 ml conical tube and then 3 ml of the pH-adjusted and filtered 100% ethanol was added to the conical tube containing 1 g of CSA-44. The tube was capped and the solution sonicated in a tub sonicator for 15 minutes, making sure the CSA/ethanol solution is below the water line of the tub sonicator. The solution was stored in a capped container at room temperature.

Preparatory Example 5

Preparation of 500 mg/ml CSA-44 in Ethanol Stock Solution

The pH of 100% ethanol was adjusted to 4.5 using 85% lactic acid and then the ethanol was filtered using a 0.22 μm syringe filter. 1 g CSA-44 was added to a 50 ml conical tube and then 3 ml of the pH-adjusted and filtered 100% ethanol was added to the conical tube containing 1 g of CSA-44. The tube was capped and the solution sonicated in a tub sonicator for 15 minutes, making sure the CSA/ethanol solution is below the water line of the tub sonicator. The solution was stored in a capped container at room temperature.

Preparatory Example 6

Preparation of 10% Pluronic F-127 Working Solution

A working aqueous solution of 10% Pluronic F-127 was made by sonicating a 10% Pluronic F-127 stock solution for at least 15 minutes in a tub sonicator at 20-23° C., filtering approximately 25 ml of the Pluronic stock solution using a 0.22 μm filter, and placing 20 ml of the stock solution into a plastic beaker or 50 ml conical tube. The pH of the Pluronic F-127 solution was adjusted to 4.5 to 5.0. The working solution was placed in a capped container and permitted to sit for at least 12 hours at 20-23° C. while being protected from light. Prior to use, the working solution was sonicated in a tub sonicator for at least 15 minutes at a temperature of 20-23°.

Preparatory Example 7

Preparation of 0.5 mg/ml CSA-44 in 10% Pluronic F-127, 20 ml Volume

A working solution containing 0.5 mg/ml CSA 44 in 10% Pluronic F-127 was made by initially sonicating a 10% Pluronic F-127 stock solution in a tub sonicator for at least 15 minutes at a temperature of 20-23° C. Approximately 25 ml of the sonicated stock solution was filtered using a 0.22 μm filter, and 20 ml of the filtered solution was placed in a plastic beaker (or 50 ml conical tube). 0.01 g of CSA-44 compound was added to the 20 ml of stock solution in the plastic beaker, and the resulting mixture was sonicated in a tub sonicator for at least 15 minutes at a temperature of 20-23° C. The pH of the mixture was adjusted to 4.5-5.0. The working solution was placed in a capped container and permitted to sit for at least 12 hours at 20-23° C. while being protected from light. Prior to use, the working solution was sonicated in a tub sonicator for at least 15 minutes at a temperature of 20-23°.

Preparatory Example 8

Preparation of 1 mg/ml CSA-44 in 10% Pluronic F-127, 20 ml Volume

A working solution containing 1 mg/ml CSA 44 in 10% Pluronic F-127 was made by initially sonicating a 10% Pluronic F-127 stock solution in a tub sonicator for at least 15 minutes at a temperature of 20-23° C. Approximately 25 ml of the sonicated stock solution was filtered using a 0.22 µm filter, and 20 ml of the filtered solution was placed in a plastic beaker (or 50 ml conical tube). 0.02 g of CSA-44 compound was added to the 20 ml of stock solution in the plastic beaker, and the resulting mixture was sonicated in a tub sonicator for at least 15 minutes at a temperature of 20-23° C. The pH of the mixture was adjusted to 4.5-5.0. The working solution was placed in a capped container and permitted to sit for at least 12 hours at 20-23° C. while being protected from light. Prior to use, the working solution was sonicated in a tub sonicator for at least 15 minutes at a temperature of 20-23°.

Preparatory Example 9

Preparation of 15 mg/ml CSA-44 in 10% Pluronic F-127, 20 ml Volume

A working solution containing 15 mg/ml CSA 44 in 10% Pluronic F-127 was made by initially sonicating a 10% Pluronic F-127 stock solution in a tub sonicator for at least 15 minutes at a temperature of 20-23° C. Approximately 25 ml of the sonicated stock solution was filtered using a 0.22 µm filter, and 20 ml of the filtered solution was placed in a plastic beaker (or 50 ml conical tube). 0.3 g of CSA-44 compound was added to the 20 ml of stock solution in the plastic beaker, and the resulting mixture was sonicated in a tub sonicator for at least 15 minutes at a temperature of 20-23° C. The pH of the mixture was adjusted to 4.5-5.0. The working solution was placed in a capped container and permitted to sit for at least 12 hours at 20-23° C. while being protected from light. Prior to use, the working solution was sonicated in a tub sonicator for at least 15 minutes at a temperature of 20-23°.

Preparatory Example 10

Preparation of 30 mg/ml CSA-44 in 10% Pluronic F-127, 20 ml Volume

A working solution containing 30 mg/ml CSA 44 in 10% Pluronic F-127 was made by initially sonicating a 10% Pluronic F-127 stock solution in a tub sonicator for at least 15 minutes at a temperature of 20-23° C. Approximately 25 ml of the sonicated stock solution was filtered using a 0.22 µm filter, and 20 ml of the filtered solution was placed in a plastic beaker (or 50 ml conical tube). 0.6 g of CSA-44 compound was added to the 20 ml of stock solution in the plastic beaker, and the resulting mixture was sonicated in a tub sonicator for at least 15 minutes at a temperature of 20-23° C. The pH of the mixture was adjusted to 4.5-5.0. The working solution was placed in a capped container and permitted to sit for at least 12 hours at 20-23° C. while being protected from light. Prior to use, the working solution was sonicated in a tub sonicator for at least 15 minutes at a temperature of 20-23°.

Preparatory Example 11

Preparation of 6 mg/ml CSA-44 in 0.1% Tween 20 and 1% HEC 90,000 MW, 20 ml Volume A working solution was made by initially sonicating 2% HEC stock solution (filtered and spun) and 20% Tween 20 stock solution (filtered) for 15 minutes. 10.17 ml of the filtered and spun 2% HEC stock solution was combined with 9.83 ml double distilled water (filtered using 0.22 µm filter) to create 20 ml of 1.017% HEC solution. 0.101 ml was removed from the 20 ml of 1.017% HEC solution, and 0.101 ml of the filtered 20% Tween 20 stock solution was added to the remaining 1.017% HEC solution to yield a Tween 20/HEC solution. The Tween 20/HEC solution and a 500 mg/ml CSA-44 stock solution were sonicated in a tub sonicator for 15 minutes. 0.24 ml was removed from the sonicated Tween 20/HEC solution, and 0.24 ml of the sonicated 500 mg/ml CSA-44 stock solution was added to the remaining Tween 20/HEC solution to yield a solution containing 6 mg/ml CSA-44 in 0.1% Tween 20 and 1% HEC 90. The CSA/Tween 20/HEC solution was tub sonicated for 15 minutes, the pH was adjusted to 4.5 using 1M and 0.1M NaOH, and the resulting solution was stored in a capped container at room temperature.

Preparatory Example 12

Preparation of 10 mg/ml CSA-44 in 1.5% Tween 20 and 1% HEC 90,000 MW, 20 ml Volume A working solution was made by initially sonicating 2% HEC stock solution (filtered and spun) and 20% Tween 20 stock solution (filtered) in a tub sonicator for 15 minutes. 10.206 ml of the filtered and spun 2% HEC stock solution was combined with 7.794 ml double distilled water (filtered using 0.22 µm filter) to create 18 ml of 1.134% HEC solution. 0.363 ml was removed from the 18 ml of 1.134% HEC solution, and 1.563 ml of the filtered 20% Tween 20 stock solution was added to the remaining 1.134% HEC solution to yield a Tween 20/HEC solution. The Tween 20/HEC solution and a 250 mg/ml CSA-44 stock solution were each sonicated in a tub sonicator for 15 minutes. 0.8 ml of the sonicated 250 mg/ml CSA-44 stock solution was added to the Tween 20/HEC solution to yield a solution containing 10 mg/ml CSA-44 in 1.5% Tween 20 and 1% HEC 90. The CSA/Tween 20/HEC solution was tub sonicated for 15 minutes, the pH was adjusted to 4.5 using 1M and 0.1M NaOH, and the resulting solution was stored in a capped container at room temperature.

Test Samples 1-67

Raw test data for Test Samples 1-67 are set forth in Exhibit 1 of the Appendix and also raw data sheets. Data relating to Test Samples 1-67 are summarized in the following Tables.

TABLE 1

| COMPONENT | 1 (1a) | 2 (2a) | 3 (3a) | 4 (4a) | 5 (5a) | 5 (5b) | 6 (6a) |
|---|---|---|---|---|---|---|---|
| CSA (mg/ml) | 6 | 6 | 6 | 6 | 6 | 6 | 6 |
| CSA Solvent | Saline | Saline | Saline | Saline | Saline | Saline | Saline |
| Pluronic F-127 (%) | 1.5 | 1.5 | 1.5 | 1.5 | 3 | 3 | 3 |
| Tween 80 (%) | 0 | 0 | 0 | 0 | 0 | 0 | 0 |
| Tween 20 (%) | 0 | 0 | 0 | 0 | 0 | 0 | 0 |
| Methocel (%) | 0 | 0 | 0 | 0 | 0 | 0 | 0 |
| Hydroxyethyl cellulose (%) | 0 | 0 | 0 | 0 | 0 | 0 | 0 |
| pH | 4.50 | 4.50 | 4.50 | 4.50 | 4.50 | 4.50 | 4.50 |
| Acid Adjuster | Lactic | Lactic | Lactic | Acetic | Acetic | Acetic | Lactic |
| Temperature (° C.) | 4 | 25 | 25 | 25 | 25 | 25 | 25 |
| Sonication | Tub | Tub | Tub | Tub | Tub | Tub | Tub |
| Avg Size (nm) | 7120.9 | 7453.1 | 5343.4 | 2076.6 | 14.3 | 23.9 | 13.6 |

TABLE 2

| COMPONENT | 7 (7a) | 7 (7b) | 8 (8a) | 9 (9a) | 9 (9b) | 9 (9c) | 10(10a) |
|---|---|---|---|---|---|---|---|
| CSA (mg/ml) | 6 | 6 | 6 | 6 | 6 | 6 | 6 |
| CSA Solvent | F-127 | F-127 | Water | F-127 | F-127 | F-127 | F-127 |
| Pluronic F-127 (%) | 6 | 6 | 0 | 6 | 6 | 6 | 6 |
| Tween 80 (%) | 0 | 0 | 0.5 | 0 | 0 | 0 | 0 |
| Tween 20 (%) | 0 | 0 | 0 | 0 | 0 | 0 | 0 |
| Methocel (%) | 0 | 0 | 0 | 0 | 0 | 0 | 0 |
| Hydroxyethyl cellulose (%) | 0 | 0 | 0 | 0 | 0 | 0 | 0 |
| pH | 4.51 | 4.51 | 4.52 | 4.53 | 4.51 | 4.53 | 4.51 |
| Acid Adjuster | Lactic | Lactic | Lactic | Lactic | Lactic | Lactic | Lactic |
| Temperature (° C.) | 25 | 25 | 25 | 25 | 25 | 25 | 25 |
| Sonication | Tub | Tub | Tub | High | High | High | Low |
| Avg Size (nm) | 11.4 | 18.6 | 8000.9 | 18.5 | 23.9 | 15.0 | 12.5 |

TABLE 3

| COMPONENT | 10 (10b) | 11 | 12 | 13 | 14 (14a) | 15 (15a) | 16 |
|---|---|---|---|---|---|---|---|
| CSA (mg/ml) | 6 | 6 | 6 | 6 | 6 | 6 | 6 |
| CSA Solvent | F-127 | Water | Water | Water | Ethanol (100%) | Ethanol (100%) | Water |
| Pluronic F-127 (%) | 6 | 0 | 0 | 0 | 0 | 0 | 0 |
| Tween 80 (%) | 0 | 0.025 | 0.05 | 0.025 | 0.025 | 0 | 0 |
| Tween 20 (%) | 0 | 0 | 0 | 0 | 0 | 0 | 0 |
| Methocel (%) | 0 | 0 | 0 | 0 | 0 | 0 | 0 |
| Hydroxyethyl cellulose (%) | 0 | 0 | 0 | 0 | 0 | 0 | 0 |
| pH | 4.51 | 4.50 | 4.51 | 4.50 | 4.50 | 4.50 | 4.51 |
| Acid Adjuster | Lactic | Lactic | Lactic | Lactic | Lactic | Lactic | Lactic |
| Temperature (° C.) | 25 | 25 | 25 | 37 | 25 | 25 | 25 |
| Sonication | Low | Tub | Tub | Tub | Tub | Tub | Tub |
| Avg Size (nm) | 28.6 | n/a | n/a | n/a | 790.8 | 157.7 | n/a |

TABLE 4

| COMPONENT | 17 (17a) | 18 | 19 (19a) | 20 (20a) | 21 (21a) | 22 (22a) | 23 (23a) |
|---|---|---|---|---|---|---|---|
| CSA (mg/ml) | 6 | 36 | 6 | 0.6 | 3 | 6 | 6 |
| CSA Solvent | Water | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 | 0 |
| Tween 80 (%) | 0 | 0 | 0 | 0 | 0 | 0 | 0 |
| Tween 20 (%) | 0 | 0 | 0.05 | 0.05 | 0.5 | 0.5 | 1.5 |

TABLE 4-continued

| COMPONENT | 17 (17a) | 18 | 19 (19a) | 20 (20a) | 21 (21a) | 22 (22a) | 23 (23a) |
|---|---|---|---|---|---|---|---|
| Methocel (%) | 0 | 0 | 0 | 0 | 0 | 0 | 0 |
| Hydroxyethyl cellulose (%) | 0 | 0 | 0 | 0 | 0 | 0 | 0 |
| pH | 4.53 | 4.25 | 4.53 | 4.54 | 4.55 | 4.55 | 4.57 |
| Acid Adjuster | Lactic | Lactic | Lactic | Lactic | Lactic | Lactic | Lactic |
| Temperature (° C.) | 25 | 25 | 25 | 25 | 25 | 25 | 25 |
| Sonication | Tub | None | Tub | Tub | Tub | Tub | Tub |
| Avg Size (nm) | 7893.5 | n/a | 15573.3 | 295.2 | 39.3 | 1141.5 | 980.3 |

TABLE 5

| COMPONENT | 24 (24a) | 25 (25a) | 26 (26a) | 27 (27a) | 28 (28a) | 29 (29a) | 30 (30a) |
|---|---|---|---|---|---|---|---|
| CSA (mg/ml) | 3 | 6 | 6 | 6 | 6 | 6 | 6 |
| CSA Solvent | Ethanol (100%) | Water | Water | Water | Water | Ethanol (100%) | Ethanol (50%) |
| Pluronic F-127 (%) | 0 | 0 | 0 | 0 | 0 | 0 | 0 |
| Tween 80 (%) | 0 | 0 | 0 | 0 | 0 | 0 | 0 |
| Tween 20 (%) | 1.5 | 0.5 | 0.05 | 0.5 | 0.05 | 0.05 | 0.05 |
| Methocel (%) | 0 | 2 | 2 | 0 | 0 | 0 | 0 |
| Hydroxyethyl cellulose (%) | 0 | 0 | 0 | 2 (250k) | 2 (250k) | 2 (250k) | 2 (250k) |
| pH | 4.53 | 4.50 | 4.50 | 4.53 | 4.51 | 4.51 | 4.57 |
| Acid Adjuster | Lactic | Lactic | Lactic | Lactic | Lactic | Lactic | Lactic |
| Temperature (° C.) | 25 | 25 | 25 | 25 | 25 | 25 | 25 |
| Sonication | Tub | Tub | Tub | Tub | Tub | Tub | Tub |
| Avg Size (nm) | 266.5 | 1768.5 | 124.9 | 834.5 | 38.6 | 26.7 | 27.9 |

TABLE 6

| COMPONENT | 31 (31a) | 32 (32a) | 33 (33a) | 34 (34a) | 35 (35a) | 36 (29a) | 37 (37a) |
|---|---|---|---|---|---|---|---|
| CSA (mg/ml) | 6 | 6 | 6 | 6 | 6 | 6 | 6 |
| CSA Solvent | Ethanol (100%) | Ethanol (50%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 | 0 |
| Tween 80 (%) | 0 | 0 | 0 | 0 | 0 | 0 | 0 |
| Tween 20 (%) | 0.05 | 0.05 | 0.05 | 0.05 | 0.05 | 0.05 | 0.05 |
| Methocel (%) | 0 | 0 | 0 | 0 | 0 | 0 | 0 |
| Hydroxyethyl cellulose (%) | 1 (250k) | 1 (250k) | 2 (250k) | 2 (250k) | 1 (250k) | 1 (250k) | 1 (90k) |
| pH | 4.56 | 4.52 | 4.48 | 4.51 | 4.51 | 4.50 | 4.53 |
| Acid Adjuster | Lactic | Lactic | Lactic | Lactic | Lactic | Lactic | Lactic |
| Temperature (° C.) | 25 | 25 | 25 | 25 | 25 | 25 | 25 |
| Sonication | Tub | Tub | Tub | Tub | Tub | Tub | Tub |
| Avg Size (nm) | 21.5 | 792.4 | 37.6 | 46.9 | 24.4 | 27.3 | 20.6 |

TABLE 7

| COMPONENT | 37 (37b) | 37 (37c) | 38 (38a) | 38 (38b) | 38 (38c) | 39 (29a) | 39 (39b) |
|---|---|---|---|---|---|---|---|
| CSA (mg/ml) | 6 | 6 | 6 | 6 | 6 | 6 | 6 |
| CSA Solvent | Ethanol (100%) | Ethanol (50%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 | 0 |
| Tween 80 (%) | 0 | 0 | 0 | 0 | 0 | 0 | 0 |
| Tween 20 (%) | 0.05 | 0.05 | 0.1 | 0.1 | 0.1 | 0.05 | 0.05 |
| Methocel (%) | 0 | 0 | 0 | 0 | 0 | 0 | 0 |
| Hydroxyethyl cellulose (%) | 1 (90k) | 1 (90k) | 1 (90k) | 1 (90k) | 1 (90k) | 1 (250k) | 1 (250k) |
| pH | 4.53 | 4.53 | 4.51 | 4.51 | 4.51 | 4.50 | 4.50 |
| Acid Adjuster | Lactic | Lactic | Lactic | Lactic | Lactic | Lactic | Lactic |
| Temperature (° C.) | 25 | 25 | 25 | 25 | 25 | 25 | 25 |
| Sonication | Tub | Tub | Tub | Tub | Tub | Tub | Tub |
| Avg Size (nm) | 3850.2 | 76.9 | 23.0 | 24.6 | 22.4 | 27.4 | 22.5 |

TABLE 8

| COMPONENT | SAMPLE NUMBER (DLS NAME) | | | | | | |
|---|---|---|---|---|---|---|---|
| | 40 (40a) | 41 (41a) | 42 (42a) | 43 (43a) | 44 (44a) | 45 (45a) | 46 (46a) |
| CSA (mg/ml) | 6 | 6 | 10 | 10 | 10 | 10 | 10 |
| CSA Solvent | Ethanol (100%) | Ethanol (50%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 | 0 |
| Tween 80 (%) | 0 | 0 | 0 | 0 | 0 | 0 | 0 |
| Tween 20 (%) | 0.1 | 0.5 | 0.05 | 0.5 | 1 | 1 | 1 |
| Methocel (%) | 0 | 0 | 0 | 0 | 0 | 0 | 0 |
| Hydroxyethyl cellulose (%) | 1 (250k) | 1 (90k) | 0.1 (90k) | 1 (90k) | 1 (90k) | 1.5 (90k) | 1.7 (90k) |
| pH | 4.51 | 4.51 | 4.51 | 4.51 | 4.54 | 4.53 | 4.52 |
| Acid Adjuster | Lactic | Lactic | Lactic | Lactic | Lactic | Lactic | Lactic |
| Temperature (° C.) | 25 | 25 | 25 | 25 | 25 | 25 | 25 |
| Sonication | Tub | Tub | Tub | Tub | Tub | Tub | Tub |
| Avg Size (nm) | 45.5 | 15.0 | 4850.2 | 193.4 | 16.3 | 6253.5 | 6591.0 |

TABLE 9

| COMPONENT | SAMPLE NUMBER (DLS NAME) | | | | | | |
|---|---|---|---|---|---|---|---|
| | 47 (47a) | 48 (48a) | 49 (49a) | 50 (50a) | 51 (51a) | 52 (52a) | 53 (53a) |
| CSA (mg/ml) | 10 | 6 | 0 | 10 | 10 | 10 | 10 |
| CSA Solvent | Ethanol (100%) | Ethanol (50%) | Ethanol (0.6%) | Ethanol (100%) | Ethanol (100%) | Ethanol (100%) | Ethanol (100%) |
| Pluronic F-127 (%) | 0 | 0 | 0 | 0 | 0 | 0 | 0 |
| Tween 80 (%) | 0 | 0 | 0 | 0 | 0 | 0 | 0 |
| Tween 20 (%) | 1 | 0.5 | 0.5 | 1.5 | 1.5 | 2 | 2 |
| Methocel (%) | 0 | 0 | 0 | 0 | 0 | 0 | 0 |
| Hydroxyethyl cellulose (%) | 2 (90k) | 1 (250k) | 0.1 (90k) | 0.9 (90k) | 0.9 (250k) | 0.9 (90k) | 0.9 (250k) |
| pH | 4.51 | 4.51 | 4.53 | 4.54 | 4.52 | 4.57 | 4.50 |
| Acid Adjuster | Lactic | Lactic | Lactic | | | | |
| Temperature (° C.) | 25 | 25 | 25 | 25 | 25 | 25 | 25 |
| Sonication | Tub | Tub | Tub | Tub | Tub | Tub | Tub |
| Avg Size (nm) | 6823.6 | 16.0 | 13.2 | 11.2 | 63.6 | 17.3 | 32.8 |

TABLE 10

| COMPONENT | SAMPLE NUMBER (DLS NAME) | | | | | | |
|---|---|---|---|---|---|---|---|
| | 54 (54a) | 55 (55a) | 56 (56a) | 57 (57a) | 58 (58a) | 59 | 60 |
| CSA (mg/ml) | 10 | 30 | 30 | 30 | 30 | 10 | 30 |
| CSA Solvent | Ethanol (100%) | Ethanol (100%) | Ethanol (100%) | Ethanol (100%) | Ethanol (100%) | Ethanol (100%) | Ethanol (100%) |
| Pluronic F-127 (%) | 6 | 0 | 0 | 0 | 0 | 0 | 0 |
| Tween 80 (%) | 0 | 0 | 0 | 0 | 0 | 0 | 0 |
| Tween 20 (%) | 0 | 3 | 3 | 6 | 6 | 0 | 3 |
| Methocel (%) | 0 | 0 | 0 | 0 | 0 | 0 | 0 |
| Hydroxyethyl cellulose (%) | 0 | 1 (90k) | 1.5 (90k) | 1 (90k) | 1.5 (90k) | 0 | 0 |
| pH | 4.53 | 4.57 | 4.55 | 4.53 | 4.52 | 4.48 | 4.52 |
| Acid Adjuster | | | | | | | |
| Temperature (° C.) | 25 | 25 | 25 | 25 | 25 | 25 | 25 |
| Sonication | Tub | Tub | Tub | Tub | Tub | Tub | Tub |
| Avg Size (nm) | 8.8 | 10379.2 | 17158.5 | 16258.0 | 17158.5 | n/a | n/a |

TABLE 11

| COMPONENT | SAMPLE NUMBER (DLS NAME) | | | | | | |
|---|---|---|---|---|---|---|---|
| | 61 (61a) | 62 (62a) | 63 (63a) | 64 (64a) | 65 (65a) | 66 (66a) | 67 (67a) |
| CSA (mg/ml) | 30 | 10 | 10 | 6 | 6 | 0 | 6 |
| CSA Solvent | Ethanol (100%) | Ethanol (100%) | | Ethanol (100%) | Ethanol (100%) | | |
| Pluronic F-127 (%) | 0 | 10 | 10 | 0 | 0 | 10 | 10 |
| Tween 80 (%) | 0 | 0 | 0 | 0 | 0 | 0 | 0 |
| Tween 20 (%) | 6 | 0 | 0 | 1 | 1.5 | 0 | 0 |
| Methocel (%) | 0 | 0 | 0 | 0 | 0 | 0 | 0 |

TABLE 11-continued

| COMPONENT | 61 (61a) | 62 (62a) | 63 (63a) | 64 (64a) | 65 (65a) | 66 (66a) | 67 (67a) |
|---|---|---|---|---|---|---|---|
| Hydroxyethyl cellulose (%) | 0 | 0 | 0 | 1 (90k) | 1 (90k) | 1 (90k) | 1 (90k) |
| pH | 4.53 | 4.52 | 4.49 | 4.58 | 4.50 | 4.48 | 4.51 |
| Acid Adjuster | | | | | | | |
| Temperature (° C.) | 25 | 25 | 25 | 25 | 25 | 25 | 25 |
| Sonication | Tub | Tub | Tub | Tub | Tub | Tub | Tub |
| Avg Size (nm) | 11.9 | 15.5 | 2.2 | 17.4 | 14.2 | 19.6 | 13.4 |

Comparative test data for several of Test Examples 1-67 are set forth in Exhibit 2 of the Appendix. A summary of the comparative test data are set forth in the following Tables.

Tables 12 and 13 show data that compare the affect of solute on solubility and particle size. The pH for all samples was rounded to 4.5. "Dust" can refer to either contaminants or large agglomerates of CSA or micelle-forming agent.

TABLE 12

| COMPONENT | DLS NAME | | | | | |
|---|---|---|---|---|---|---|
| | 14a | 15a | 17a | 19a | 54a | 62a |
| CSA (mg/ml) | 6 | 6 | 6 | 6 | 10 | 10 |
| CSA Solvent | Ethanol (100%) | Ethanol (100%) | Water (ddw) | Ethanol (100%) | Ethanol (100%) | Ethanol (100%) |
| Pluronic F-127 (%) | 0 | 0 | 0 | 0 | 6 | 10 |
| Tween 80 (%) | 0.025 | 0 | 0 | 0 | 0 | 0 |
| Tween 20 (%) | 0 | 0 | 0 | 0.05 | 0 | 0 |
| Methocel (%) | 0 | 0 | 0 | 0 | 0 | 0 |
| Hydroxyethyl cellulose (%) | 0 | 0 | 0 | 0 | 0 | 0 |
| Acid Adjuster | lactic | lactic | lactic | lactic | lactic | lactic |
| Temperature (° C.) | 25 | 25 | 25 | 25 | 25 | 25 |
| Sonication | Tub | Tub | Tub | Tub | Tub | Tub |
| Particle Size Range (nm) | 700-800 | 150-160 | | | 6-13 | 13-19 |
| Mean Particle Size (μm) | | | 4.5-14.5 | 4-30 | | |
| Baseline Error (%) | 0-3 | 0.5-1.0 | 150-275 | 160-280 | 0-5 | 0-2 |
| Dust (%) | 0-3 | 0-4 | 0 | 0 | 0-8 (31) | 0-25 |

TABLE 13

| COMPONENT | DLS NAME or SAMPLE NUMBER | | | | |
|---|---|---|---|---|---|
| | 07a | 63a | 66 | 08a | 49a |
| CSA (mg/ml) | 6 | 10 | 0 | 6 | 0 |
| CSA Solvent | F-127 | F-127 | F-127 | Water (ddw) | Ethanol (100%) |
| Pluronic F-127 (%) | 6 | 10 | 10 | 0 | 0 |
| Tween 80 (%) | 0 | 0 | 0 | 0.5 | 0 |
| Tween 20 (%) | 0 | 0 | 0 | 0 | 0.5 |
| Methocel (%) | 0 | 0 | 0 | 0 | 0 |
| Hydroxyethyl cellulose (%) | 0 | 0 | 1 (90k) | 0 | 1 (90k) |
| Acid Adjuster | lactic | lactic | lactic | lactic | lactic |
| Temperature (° C.) | 25 | 25 | 25 | 25 | 25 |
| Sonication | Tub | Tub | Tub | Tub | Tub |
| Particle Size Range (nm) | 9-15 | 1-4 | 18-29 | | 12-20 |
| Mean Particle Size (μm) | | | | 2-11 | |
| Baseline Error (%) | <1; 57 | 0-2 | 1-3 | 250-1000 | 0-2 |
| Dust (%) | 0-10 | 10-31 | 9-26 | 50-60 | 0-30 |

Tables 14 and 15 show data that compare the affects of solute on solubility and sonication and temperature on particle size and stability. The pH for all samples was rounded to 4.5. "Dust" can refer to either contaminants or large agglomerates of CSA or micelle-forming agent.

TABLE 14

| COMPONENT | DLS NAME | | | | | |
|---|---|---|---|---|---|---|
| | 01a | 02a | 03a | 04a | 05a | 05b-day 5 |
| CSA (mg/ml) | 6 | 6 | 6 | 6 | 6 | 6 |
| CSA Solvent | Saline | Saline | Saline | Saline | Saline | Saline |
| Pluronic F-127 (%) | 1.5 | 1.5 | 1.5 | 1.5 | 3 | 3 |
| Tween 80 (%) | 0.025 | 0 | 0 | 0 | 0 | 0 |
| Tween 20 (%) | 0 | 0 | 0 | 0.05 | 0 | 0 |
| Methocel (%) | 0 | 0 | 0 | 0 | 0 | 0 |
| Hydroxyethyl cellulose (%) | 0 | 0 | 0 | 0 | 0 | 0 |
| Acid Adjuster | lactic | lactic | lactic | acetic | acetic | acetic |
| Temperature (° C.) | 4 | 4 | 25 | 25 | 25 | 25 |
| Sonication | Tub | Tub | Tub | Tub | Tub | Tub |
| Particle Size Range (nm) | | | | | 13-16 | 15-30 |
| Mean Particle Size (μm) | 5.5-8.0 | 6.0-8.5 | 3.3-7.2 | 1.8-2.2 | | |
| Baseline Error (%) | 20-140 | 35-130 | 25-45 | 25-46 | 3-14 | 10-300 |
| Dust (%) | 50-60 | 50-60 | 30-50 | 25-40 | 0 (7.5) | 0 (23) |

TABLE 15

| COMPONENT | DLS NAME or SAMPLE NUMBER | | | | | |
|---|---|---|---|---|---|---|
| | 06a | 07a | 09a | 09b-day 1 | 10a | 10b-day1 |
| CSA (mg/ml) | 6 | 6 | 6 | 6 | 6 | 6 |
| CSA Solvent | Saline | F-127 | F-127 | F-127 | F-127 | F-127 |
| Pluronic F-127 (%) | 3 | 6 | 6 | 6 | 6 | 6 |
| Tween 80 (%) | 0 | 0 | 0 | 0 | 0 | 0 |
| Tween 20 (%) | 0 | 0 | 0 | 0 | 0 | 0 |
| Methocel (%) | 0 | 0 | 0 | 0 | 0 | 0 |
| Hydroxyethyl cellulose (%) | 0 | 0 | 0 | 0 | 0 | 0 |
| Acid Adjuster | lactic | lactic | lactic | lactic | lactic | lactic |
| Temperature (° C.) | 25 | 25 | 25 | 25 | 25 | 25 |
| Sonication | Tub | Tub | hi probe | hi probe | low probe | low probe |
| Particle Size Range (nm) | 12-15 | 9-15 | 15-25 | 18-30 | 10-15 | 15-35 |
| Mean Particle Size (μm) | | | | | | |
| Baseline Error (%) | 3-20 | <1; 57 | 0-12 | 1-18 | 1-12 | 2-160 |
| Dust (%) | 0-12 | 0-10 | 0 | 0-12 (44) | 0 (8.6) | 0-25 |

Tables 16-18 show data that compare the affects of methylcellulose or hydroxyethyl cellulose with more or less Tween 20 on solubility, stability, and particle size. The pH for all samples was rounded to 4.5. "Dust" can refer to either contaminants or large agglomerates of CSA or micelle-forming agent.

TABLE 16

| COM-PONENT | DLS NAME | | | | | |
|---|---|---|---|---|---|---|
| | 19a | 20a | 21a | 22a | 23a | 24a |
| CSA (mg/ml) | 6 | 0.6 | 3 | 6 | 6 | 3 |
| CSA Solvent | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 |
| Tween 80 (%) | 0 | 0 | 0 | 0 | 0 | 0 |
| Tween 20 (%) | 0.05 | 0.05 | 0.5 | 0.5 | 1.5 | 1.5 |
| Methocel (%) | 0 | 0 | 0 | 0 | 0 | 0 |
| Hydroxyethyl cellulose (%) | 0 | 0 | 0 | 0 | 0 | 0 |
| Acid Adjuster | lactic | lactic | lactic | lactic | lactic | lactic |
| Temperature (° C.) | | | | | | |
| Sonication | | | | | | |
| Particle Size Range (nm) | | 100-500 | 4-75 | | 900-1000 | 250-280 |
| Mean Particle Size (μm) | 4-30 | | | 1-1.5 | | |
| Baseline Error (%) | 160-280 | 20-85 | 4-6 | 2-4 | 0-1 | 0-2 |
| Dust (%) | 0 | 0-20 | 50-55 | 15-30 | 1-8 | 9-12 |

TABLE 17

| COMPONENT | DLS NAME or SAMPLE NUMBER | | | | | |
|---|---|---|---|---|---|---|
| | 25a | 26a | 27a | 28a | 29a | 30a |
| CSA (mg/ml) | 6 | 6 | 6 | 6 | 6 | 6 |
| CSA Solvent | Water (ddw) | Water (ddw) | Water (ddw) | Water (ddw) | Ethanol (100%) | Ethanol (50%) |
| Pluronic F-127 (%) | 0 | 0 | 0 | 0 | 0 | 0 |
| Tween 80 (%) | 0 | 0 | 0 | 0 | 0 | 0 |
| Tween 20 (%) | 0.5 | 0.05 | 0.5 | 0.05 | 0.05 | 0.05 |
| Methocel (%) | 2 | 2 | 0 | 0 | 0 | 0 |
| Hydroxyethyl cellulose (%) | 0 | 0 | 2 (250k) | 2 (250k) | 2 (250k) | 2 (250k) |
| Acid Adjuster | lactic | lactic | lactic | lactic | lactic | lactic |
| Temperature (° C.) | | | | | | |
| Sonication | | | | | | |
| Particle Size Range (nm) | | 40-300 | 40-1500 | 30-45 | 25-32 | 18-25 |
| Mean Particle Size (μm) | 0.7-3 | | | | | |
| Baseline Error (%) | 12-200 | 3-250 | 50-200 | 5-60 | 2-5 | 2-4 |
| Dust (%) | 0-12 | 0-5 | 0 | 0 | 15-50 | 15-30 |

TABLE 18

| COMPONENT | DLS NAME or SAMPLE NUMBER | | | | |
|---|---|---|---|---|---|
| | 31a | 32a | 33a | 34a | 35a |
| CSA (mg/ml) | 6 | 6 | 6 | 6 | 6 |
| CSA Solvent | Ethanol (100%) | Ethanol (50%) | Ethanol (100%) | Ethanol (100%) | Ethanol (100%) |
| Pluronic F-127 (%) | 0 | 0 | 0 | 0 | 0 |
| Tween 80 (%) | 0 | 0 | 0 | 0 | 0 |
| Tween 20 (%) | 0.05 | 0.05 | 0.05 | 0.05 | 0.05 |
| Methocel (%) | 0 | 0 | 0 | 0 | 0 |
| Hydroxyethyl cellulose (%) | 1 (250k) | 1 (250k) | 2 (250k) | 2 (250k) | 1 (250k) |
| Acid Adjuster | lactic | lactic | lactic | lactic | lactic |
| Temperature (° C.) | | | | | |
| Sonication | | | | | |
| Particle Size Range (nm) | 18-25 | | 30-40 | 40-50 | 20-30 |
| Mean Particle Size (μm) | | .07-2200 | | | |
| Baseline Error (%) | 12-200 | 3-250 | 50-200 | 5-60 | 2-5 |
| Dust (%) | 0-12 | 0 | 0-10 | n/a | 0 |

Tables 19-23 show data that compare the affects of hydroxyethyl cellulose and Tween 20 on solubility, stability, and particle size. The pH for all samples was rounded to 4.5. "Dust" can refer to either contaminants or large agglomerates of CSA or micelle-forming agent.

TABLE 19

| COMPONENT | DLS NAME | | | | | |
|---|---|---|---|---|---|---|
| | 37a | 37b-day 3 | 37c-day 10 | 38a | 38b-day 3 | 38c-day 10 |
| CSA (mg/ml) | 6 | 6 | 6 | 6 | 6 | 6 |
| CSA Solvent | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 |
| Tween 80 (%) | 0 | 0 | 0 | 0 | 0 | 0 |
| Tween 20 (%) | 0.05 | 0.05 | 0.05 | 0.1 | 0.1 | 0.1 |
| Methocel (%) | 0 | 0 | 0 | 0 | 0 | 0 |
| Hydroxyethyl cellulose (%) | 1 (90k) | 1 (90k) | 1 (90k) | 1 (90k) | 1 (90k) | 1 (90k) |
| Acid Adjuster | lactic | lactic | lactic | lactic | lactic | lactic |
| Temperature (° C.) | | | | | | |
| Sonication | | | | | | |
| Particle Size Range (nm) | 18-23 | | 25-150 | 20-25 | 22-27 | 20-24 |
| Mean Particle Size (μm) | | 0.7-1.1 | | | | |
| Baseline Error (%) | 0-8 | 50-500 | 5-200 | 1-3 | 0-7 | 0-2 |
| Dust (%) | 0, (51) | 0, (57) | 0, (65) | 0, (15) | 0 | 0-10 |

TABLE 20

| COMPONENT | DLS NAME or SAMPLE NUMBER | | | | | |
|---|---|---|---|---|---|---|
| | 39a | 39b-day 10 | 40a | 41a | 41b-day 6 | 42a |
| CSA (mg/ml) | 6 | 6 | 6 | 6 | 6 | 10 |
| CSA Solvent | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 |
| Tween 80 (%) | 0 | 0 | 0 | 0 | 0 | 0 |
| Tween 20 (%) | 0.05 | 0.05 | 0.1 | 0.5 | 0.5 | 0.05 |
| Methocel (%) | 0 | 0 | 0 | 0 | 0 | 0 |
| Hydroxyethyl cellulose (%) | 1 (250k) | 1 (250k) | 1 (250k) | 1 (90k) | 1 (90k) | 0.1 (90k) |
| Acid Adjuster | lactic | lactic | lactic | lactic | lactic | lactic |
| Temperature (° C.) | | | | | | |
| Sonication | | | | | | |

TABLE 20-continued

| COMPONENT | DLS NAME or SAMPLE NUMBER | | | | | |
|---|---|---|---|---|---|---|
| | 39a | 39b-day 10 | 40a | 41a | 41b-day 6 | 42a |
| Particle Size Range (nm) | 24-30 | 20-25 | 20-60 | 14-16 | 15-30 | |
| Mean Particle Size (μm) | | | | | | 4-6 |
| Baseline Error (%) | 1-2 | 1-2 | 1-200 | 0-1 | 0-20 | 25-60 |
| Dust (%) | 0, (9) | 0-16 | 0-12 | 0 | 0-15 | 40-50 |

TABLE 21

| COMPONENT | DLS NAME or SAMPLE NUMBER | | | | | |
|---|---|---|---|---|---|---|
| | 43a | 44a | 45a | 46a | 47a | 48a |
| CSA (mg/ml) | 10 | 10 | 10 | 10 | 10 | 10 |
| CSA Solvent | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 |
| Tween 80 (%) | 0 | 0 | 0 | 0 | 0 | 0 |
| Tween 20 (%) | 0.5 | 1 | 1 | 1 | 1 | 0.5 |
| Methocel (%) | 0 | 0 | 0 | 0 | 0 | 0 |
| Hydroxyethyl cellulose (%) | 1 (90k) | 1 (90k) | 1.5 (90k) | 1.7 (90k) | 2 (90k) | 1 (250k) |
| Acid Adjuster | lactic | lactic | lactic | lactic | lactic | lactic |
| Temperature (° C.) | | | | | | |
| Sonication | | | | | | |
| Particle Size Range (nm) | 90-370 | 12-23 | | | | 14-18 |
| Mean Particle Size (μm) | | | 4.5-9 | 3.5-10 | 2-14 | |
| Baseline Error (%) | 50-215 | 1-325 | 30-80 | 50-115 | 40-60 | 0-3 |
| Dust (%) | 0-7 | 0 | 45-60 | 45-60 | 30-60 | 0-30 |

TABLE 22

| COMPONENT | DLS NAME or SAMPLE NUMBER | | | | | |
|---|---|---|---|---|---|---|
| | 49a | 50a | 51a | 52a | 53a | 55a |
| CSA (mg/ml) | 10 | 10 | 10 | 10 | 10 | 30 |
| CSA Solvent | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 |
| Tween 80 (%) | 0 | 0 | 0 | 0 | 50 | 0 |
| Tween 20 (%) | 0.5 | 1.5 | 1.5 | 2 | 2 | 3 |
| Methocel (%) | 0 | 0 | 0 | 0 | 0 | 0 |
| Hydroxyethyl cellulose (%) | 1 (90k) | 1.5 (90k) | 1 (250k) | 1 (90k) | 1 (250k) | 1 (90k) |
| Acid Adjuster | lactic | lactic | lactic | lactic | lactic | lactic |
| Temperature (° C.) | | | | | | |
| Sonication | | | | | | |
| Particle Size Range (nm) | 8-20 | 10-12 | 60-70 | 10-30 | 30-35 | |
| Mean Particle Size (μm) | | | | | 60 | 7-13 |
| Baseline Error (%) | 0-2 | 0-2 | 0-2 | 0 (760) | 0-1 | 15-50 |
| Dust (%) | 0-30 | 0 | 4-8 | 0-8 | 10 | 50-65 |

TABLE 23

| COMPONENT | DLS NAME or SAMPLE NUMBER | | | | | |
|---|---|---|---|---|---|---|
| | 56a | 57a | 58a | 61a | 64a | 65a |
| CSA (mg/ml) | 30 | 30 | 30 | 30 | 6 | 6 |
| CSA Solvent | Ethanol (100%) | Ethanol (100%) | Ethanol (100%) | Ethanol (100%) | Ethanol (100%) | Ethanol (100%) |
| Pluronic F-127 (%) | 0 | 0 | 0 | 0 | 0 | 0 |
| Tween 80 (%) | 0 | 0 | 0 | 0 | 0 | 0 |
| Tween 20 (%) | 3 | 6 | 6 | 6 | 1 | 1.5 |
| Methocel (%) | 0 | 0 | 0 | 0 | 0 | 0 |
| Hydroxyethyl cellulose (%) | 1.5 (90k) | 1 (90k) | 1.5 (90k) | 0 | 1 (90k) | 1 (90k) |
| Acid Adjuster | lactic | lactic | lactic | lactic | lactic | lactic |
| Temperature (° C.) | | | | | | |
| Sonication | | | | | | |
| Particle Size Range (nm) | | | | 11-12 | 15-20 | 13-16 |
| Mean Particle Size (μm) | 14-19 | 15-17 | 12-14 | | | |
| Baseline Error (%) | 5-20 | 25-55 | 5-13 | 2-17 | 8-40 | 0-3 |
| Dust (%) | 60-80 | 60-65 | 60-80 | 0 | 0 | 0 |

Table 24 shows data that compare the affect of Pluronic F-127 on solubility, stability, and particle size. The pH for all samples was rounded to 4.5. "Dust" can refer to either contaminants or large agglomerates of CSA or micelle-forming agent.

TABLE 24

| COMPONENT | DLS NAME or SAMPLE NUMBER | | | | |
|---|---|---|---|---|---|
| | 54a | 62a | 63a | 66a | 67a |
| CSA (mg/ml) | 10 | 10 | 10 | 0 | 6 |
| CSA Solvent | Ethanol (100%) | Ethanol (100%) | F-127 | F-127 | Ethanol (100%) |
| Pluronic F-127 (%) | 6 | 10 | 10 | 10 | 10 |
| Tween 80 (%) | 0 | 0 | 0 | 0 | 0 |
| Tween 20 (%) | 0 | 0 | 0 | 0 | 0 |
| Methocel (%) | 0 | 0 | 0 | 0 | 0 |
| Hydroxyethyl cellulose (%) | 0 | 0 | 0 | 1 (90k) | 1 (90k) |
| Acid Adjuster | lactic | lactic | lactic | lactic | lactic |
| Temperature (° C.) | | | | | |
| Sonication | | | | | |
| Particle Size Range (nm) | 6-14 | 13-19 | 1-4 | 19-20 | 12-15 |
| Mean Particle Size (μm) | | | | | |
| Baseline Error (%) | 0-5 | 0-2 | 0-2 | 0-3 | 1-4 |
| Dust (%) | 0-32 | 0-25 | 10-30 | 9-27 | 0-42 |

The relative success of the test examples is measured by the particle size range, mean particle size, baseline error, and dust %, with smaller numbers in the various categories generally indicating greater dispersion and less agglomeration.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A CSA-containing composition comprising:
   a polar solvent or aqueous carrier;
   a plurality of cationic steroidal antimicrobial (CSA) molecules; and
   a micelle-forming agent comprising an amphiphilic compound or composition forming micelles,
   wherein the amphiphilic compound or composition forming micelles encapsulates at least a portion of the CSA molecules so that no more than 25% of the CSA molecules form agglomerates larger than 1 μm in size, and
   wherein the CSA-containing composition maintains or increases efficacy in killing microbes and reduces or minimizes cytotoxicity to mammalian cells.

2. A CSA-containing composition as in claim 1, wherein the hydrophilic solvent or aqueous carrier comprises at least one of water, hydrophilic organic solvent, surfactant, non-ionic surfactant, anionic surfactant, or hydrophilic organic liquid.

3. A CSA-containing composition as in claim 1, wherein the micelle-forming agent is selected from the group consisting of modified celluloses, modified nonionic hydroxyethyl cellulose, natural polyoxyethylene sorbitol ester, hydroxyethyl cellulose, 2-hydroxyethyl cellulose with a molecular weight between 90,000 and 750,000 and a viscosity between 50-500 cps in solutions between 1% and 5% water at temperatures between 20° C. and 25° C., modified aqueous solutions of polysorbate nonionic surfactants, polyoxyethylene sorbitan mono-, di-, and tri-($C_{12}$-$C_{18}$)-alkanoates, poloxamers, hydroxymethyl cellulose, ethyl cellulose, methyl cellulose, hydroxypropyl cellulose, carboxymethyl cellulose, alkyl triammonium methosulfate, and ceteraryloctanoate.

4. A CSA-containing composition as in claim 1, wherein the amphiphilic compound or composition comprises one or more surfactants having separate hydrophobic and hydrophilic regions.

5. A CSA-containing composition as in claim 1, wherein the micelle-forming agent encapsulates at least a portion of the CSA molecules so that no more than about 15% of the CSA molecules form agglomerates larger than 1 μm in size.

6. A CSA-containing composition as in claim 1, wherein the micelle-forming agent encapsulates at least a portion of the CSA molecules so that no more than about 25% of the CSA molecules form agglomerates larger than about 500 nm in size.

7. A CSA-containing composition as in claim 1, wherein the micelle-forming agent encapsulates at least a portion of the CSA molecules so that no more than about 25% of the CSA molecules form agglomerates larger than about 250 nm in size.

8. A CSA-containing composition as in claim 1, wherein the micelle-forming agent encapsulates at least a portion of the CSA molecules so that no more than about 25% of the CSA molecules form agglomerates larger than about 100 nm in size.

9. A CSA-containing composition as in claim 1, wherein the micelle-forming agent encapsulates at least a portion of the CSA molecules so that at least about 75% of the CSA molecules are in the form of individually encapsulated particles less than 1 μm in size.

10. A CSA-containing composition as in claim 1, wherein the micelle-forming agent encapsulates at least a portion of the CSA molecules so that at least about 75% of the CSA molecules are in the form of individually encapsulated particles less than about 500 nm in size.

11. A CSA-containing composition as in claim 1, wherein the micelle-forming agent encapsulates at least a portion of the CSA molecules so that at least about 75% of the CSA molecules are in the form of individually encapsulated particles less than about 100 nm in size.

12. A CSA-containing composition as in claim 1, wherein the CSA molecules comprise one or more compounds of Formula (I) or a pharmaceutically acceptable salt thereof:

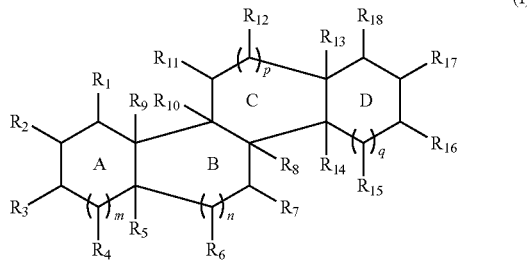

(I)

wherein
rings A, B, C, and D are independently saturated, or are fully or partially unsaturated, provided that at least two of rings A, B, C, and D are saturated;
m, n, p, and q are independently 0 or 1;
$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkyl-carboxamido, a substituted or unsubstituted di(alkyl)aminoalkyl, a substituted or unsubstituted C-carboxyalkyl, $H_2N$—$HC(Q_5)$-C(O)—O—, $H_2N$—$HC(Q_5)$-C(O)—N(H)—, a substituted or unsubstituted azidoalkyloxy, a substituted or unsubstituted cyanoalkyloxy, P.G.-HN—$HC(Q_5)$-C(O)—O—, a substituted or unsubstituted guanidine-alkyloxy, a substituted or unsubstituted quaternary ammonium alkylcarboxy, and a substituted or unsubstituted guanidinoalkyl carboxy, where $Q_5$ is a side chain of any amino acid, and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—HC$(Q_5)$-C(O)—O—, $H_2N$—$HC(Q_5)$-C(O)—N(H)—, azidoalkyloxy, cyanoalkyloxy, P.G.-HN—$HC(Q_5)$-C(O)—O—, guanidinoalkyloxy, and guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkyl-carboxyamido, a quaternary ammonium alkylcarboxy, a substituted or unsubstituted di(alkyl)aminoalkyl, a substituted or unsubstituted C-carboxyalkyl, $H_2N$—$HC(Q_5)$-C(O)—O—, $H_2N$—$HC(Q_5)$-C(O)—N(H)—, azidoalkyloxy, cyanoalkyloxy, P.G.-HN—$HC(Q_5)$-C(O)—O—, a substituted or unsubstituted guanidinoalkyloxy, and a substituted or unsubstituted guanidinoalkylcarboxy.

13. A CSA-containing composition as in claim 12, wherein
$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$) alkyl, a substituted or unsubstituted ($C_1$-$C_{18}$) hydroxyalkyl, a substituted or unsubstituted ($C_1$-$C_{18}$) alkyloxy-($C_1$-$C_{18}$) alkyl, a substituted or unsubstituted ($C_1$-$C_{18}$) alkylcarboxy-($C_1$-$C_{18}$) alkyl, a substituted or unsubstituted ($C_1$-$C_{18}$) alkylamino-($C_1$-$C_{18}$) alkyl, a substituted or unsubstituted ($C_1$-$C_{18}$) alkylamino-($C_1$-$C_{18}$) alkylamino, a substituted or unsubstituted ($C_1$-$C_{18}$) alkylamino-($C_1$-$C_{18}$) alkylamino-($C_1$-$C_{18}$) alkylamino, a substituted or unsubstituted ($C_1$-$C_{18}$)

aminoalkyl, a substituted or unsubstituted aryl, a substituted or unsubstituted arylamino-($C_1$-$C_{18}$) alkyl, a substituted or unsubstituted ($C_1$-$C_{18}$) haloalkyl, a substituted or unsubstituted $C_2$-$C_6$ alkenyl, a substituted or unsubstituted $C_2$-$C_6$ alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, a substituted or unsubstituted ($C_1$-$C_{18}$) aminoalkylcarboxy, a substituted or unsubstituted ($C_1$-$C_{18}$) aminoalkyl-aminocarbonyl, a substituted or unsubstituted ($C_1$-$C_{18}$) amino-alkylcarboxamido, a substituted or unsubstituted di($C_1$-$C_{18}$ alkyl)aminoalkyl, a substituted or unsubstituted C-carboxy($C_1$-$C_{18}$) alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC($Q_5$)-C(O)—O—, a substituted or unsubstituted ($C_1$-$C_{18}$) guanidine-alkyloxy, a substituted or unsubstituted ($C_1$-$C_{18}$) quaternary ammonium alkylcarboxy, and a substituted or unsubstituted ($C_1$-$C_{18}$) guanidinoalkyl carboxy, where $Q_5$ is a side chain of any amino acid, and P.G. is an amino protecting group;

$R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, a substituted or unsubstituted ($C_1$-$C_{18}$) hydroxyalkyl, a substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, a substituted or unsubstituted ($C_1$-$C_{18}$) haloalkyl, a substituted or unsubstituted ($C_2$-$C_6$) alkenyl, a substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, a substituted or unsubstituted di($C_1$-$C_{18}$ alkyl)aminoalkyl, a substituted or unsubstituted C-carboxy($C_1$-$C_{18}$) alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC($Q_5$)-C(O)—O—, a substituted or unsubstituted ($C_1$-$C_{18}$) guanidinoalkyloxy, and ($C_1$-$C_{18}$) guanidinoalkylcarboxy, where $Q_5$ is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, a substituted or unsubstituted ($C_1$-$C_{18}$) alkylcarboxy-($C_1$-$C_{18}$) alkyl, a substituted or unsubstituted alkylamino-($C_1$-$C_{18}$) alkylamino, a substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkyl-aminocarbonyl, a substituted or unsubstituted ($C_1$-$C_{18}$) aminoalkylcarboxyamido, a substituted or unsubstituted ($C_1$-$C_{18}$) quaternary ammonium alkylcarboxy, a substituted or unsubstituted di($C_1$-$C_{18}$ alkyl)aminoalkyl, a substituted or unsubstituted C-carboxy($C_1$-$C_{18}$) alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC($Q_5$)-C(O)—O—, a substituted or unsubstituted ($C_1$-$C_{18}$) guanidinoalkyloxy, and a substituted or unsubstituted ($C_1$-$C_{18}$) guanidinoalkylcarboxy.

14. A CSA-containing composition as in claim 12, wherein the compound of Formula (I) or pharmaceutically acceptable salt thereof comprises a compound of Formula (IA):

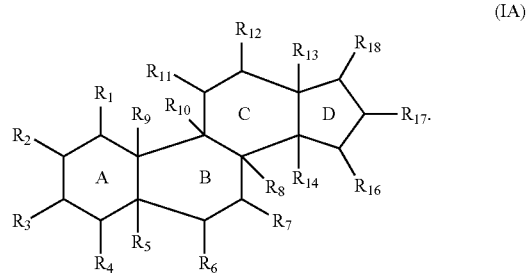

(IA)

15. A CSA-containing composition as in claim 12, wherein each of rings A, B, C, and D is independently saturated.

16. A CSA-containing composition as in claim 12, wherein $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarbox-amido, an unsubstituted di($C_1$-$C_{18}$ alkyl)aminoalkyl, unsubstituted C-carboxy($C_1$-$C_{18}$) alkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

17. A CSA-containing composition as in claim 12, wherein $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$) alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-

$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkyl-carboxamido, an unsubstituted di($C_1$-$C_5$ alkyl)amino-($C_1$-$C_5$) alkyl, unsubstituted C-carboxy($C_1$-$C_{18}$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

18. A CSA-containing composition as in claim 12, wherein $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

19. A CSA-containing composition as in claim 12, wherein $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

20. A CSA-containing composition as in claim 12, wherein
$R_3$, $R_7$, and $R_{12}$ are independently selected from the group consisting of aminoalkyloxy and aminoalkylcarboxy; and
$R_{18}$ is selected from the group consisting of alkylaminoalkyl; alkoxycarbonylalkyl; alkylcarbonyloxyalkyl; di(alkyl)aminoalkyl; C-carboxyalkyl; alkylaminoalkyl; alkyoxycarbonylalkyl; and alkylcarboxyalkyl.

21. A CSA-containing composition as in claim 12, wherein $R_3$, $R_7$, and $R_{12}$ are the same.

22. A CSA-containing composition as in claim 12, wherein $R_3$, $R_7$, and $R_{12}$ are aminoalkyloxy or aminoalkylcarboxy.

23. A CSA-containing composition as in claim 12, wherein $R_{18}$ is alkylaminoalkyl, alkoxycarbonylalkyl, di(alkyl)aminoalkyl, or alkylcarboxyalkyl.

24. A CSA-containing composition as in claim 12, wherein $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; C-carboxy-$C_4$-alkyl; $C_{13}$-alkylamino-$C_5$-alkyl; $C_6$-alkoxy-carbonyl-$C_4$-alkyl; and $C_6$-alkyl-carboxy-$C_4$-alkyl.

25. A CSA-containing composition as in claim 12, wherein the compound of Formula (I) or pharmaceutically acceptable salt thereof comprises a compound of Formula (IB) or a pharmaceutically acceptable salt thereof:

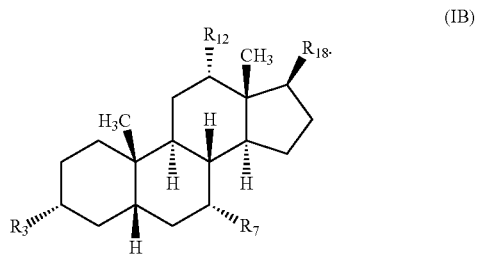

(IB)

26. A CSA-containing composition as in claim 25, wherein the compound of Formula (IB) or pharmaceutically acceptable salt thereof comprises at least one member selected from the group of:

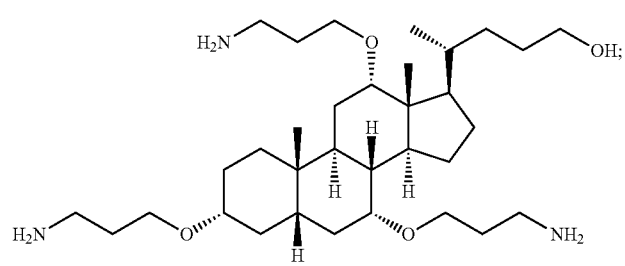

(CSA-8)

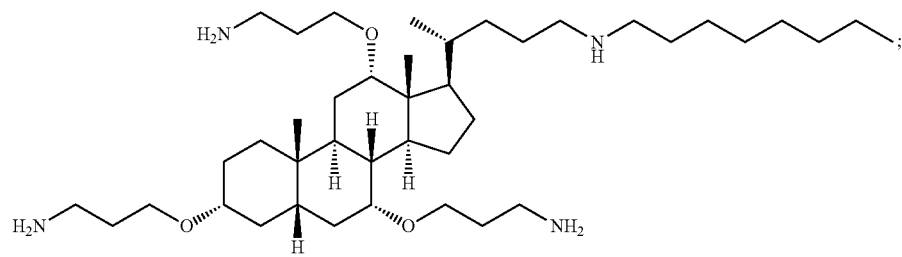

(CSA-13)

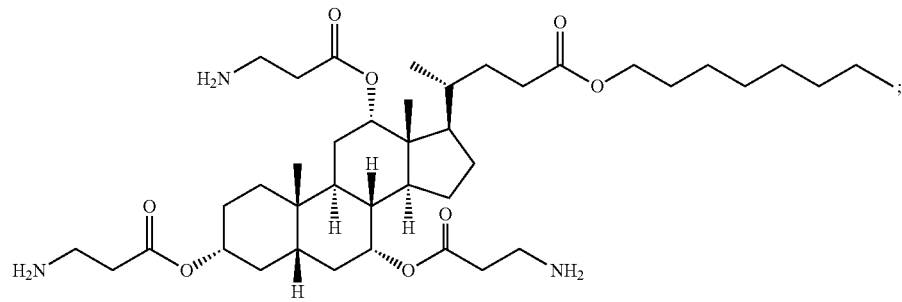

(CSA-44)

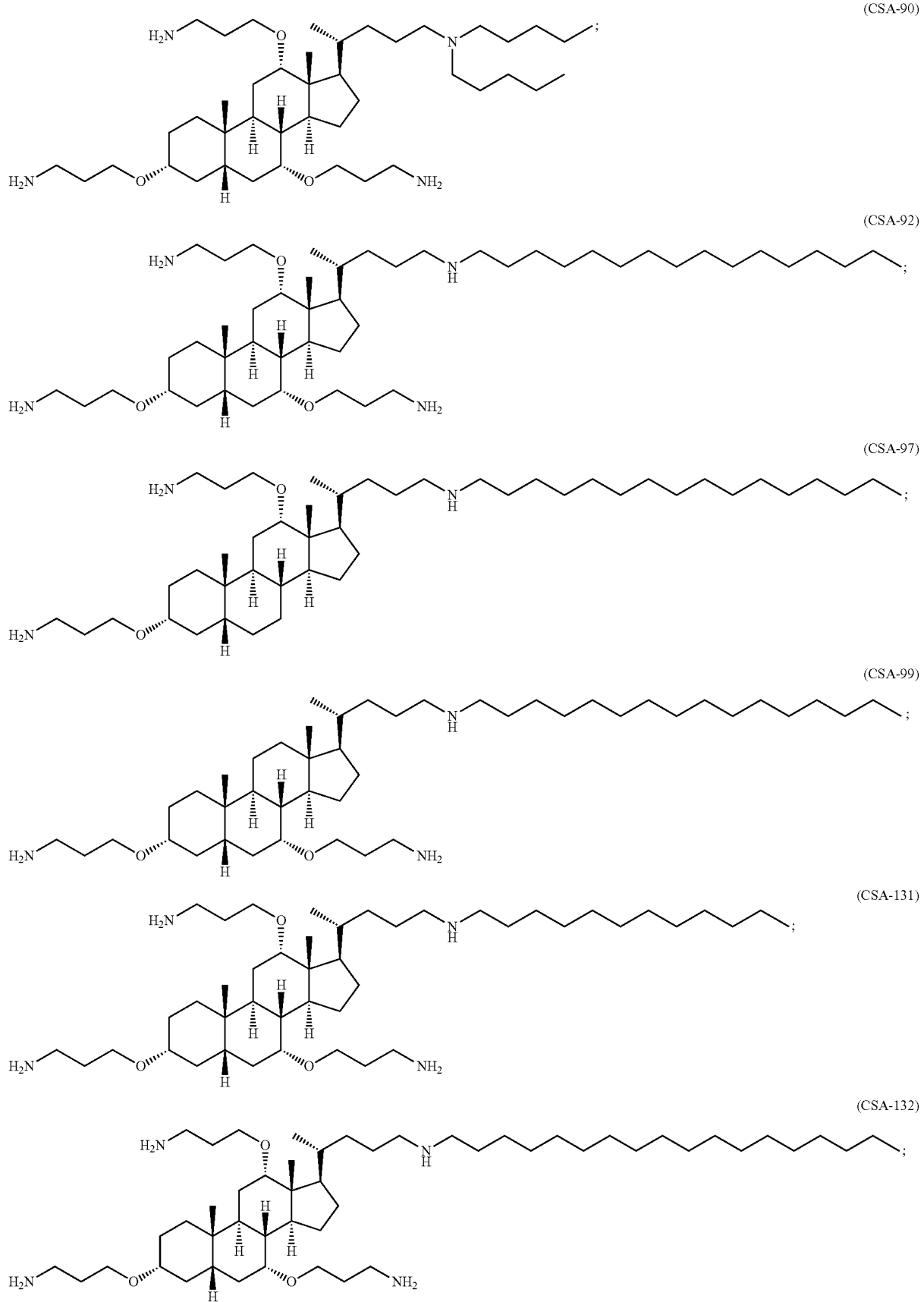

-continued
(CSA-133)
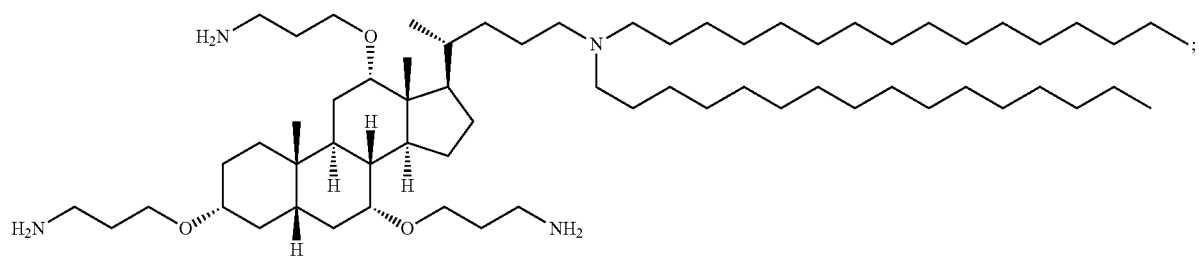
(CSA-134)
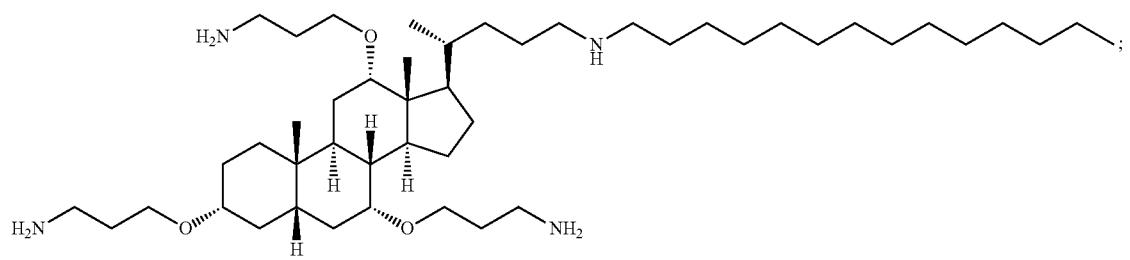
(CSA-136)
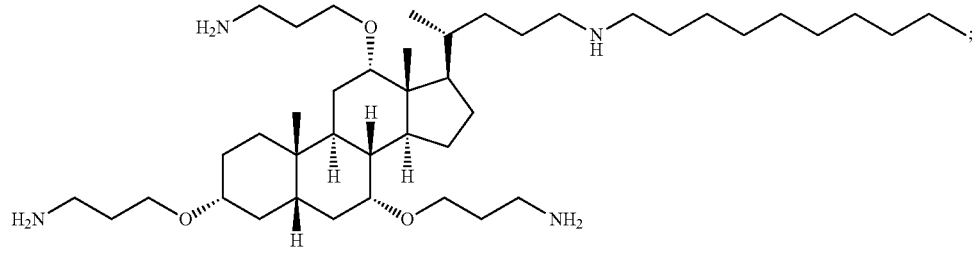
(CSA-137)
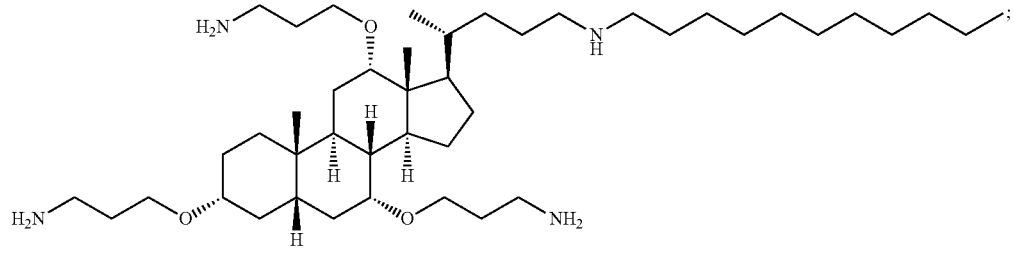
(CSA-138)
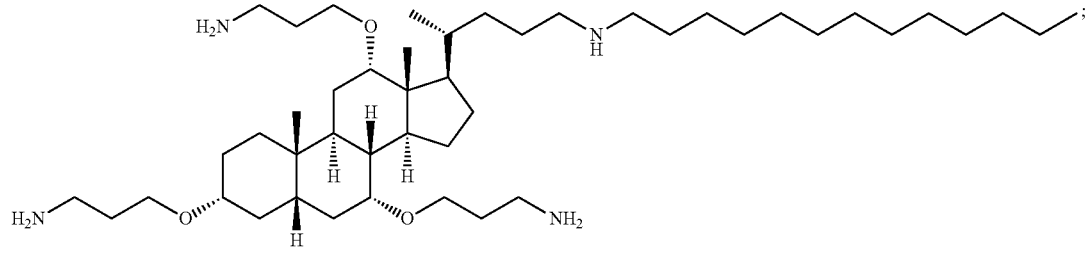
(CSA-142)
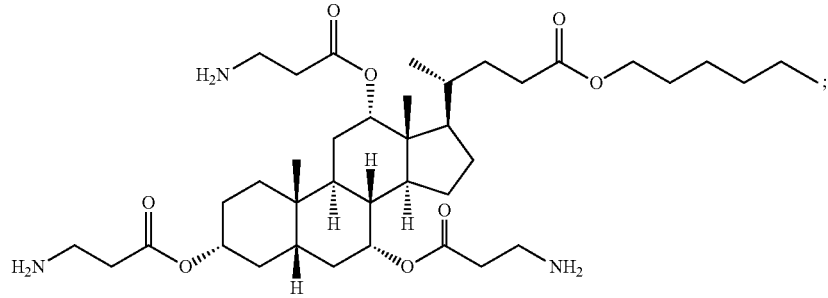

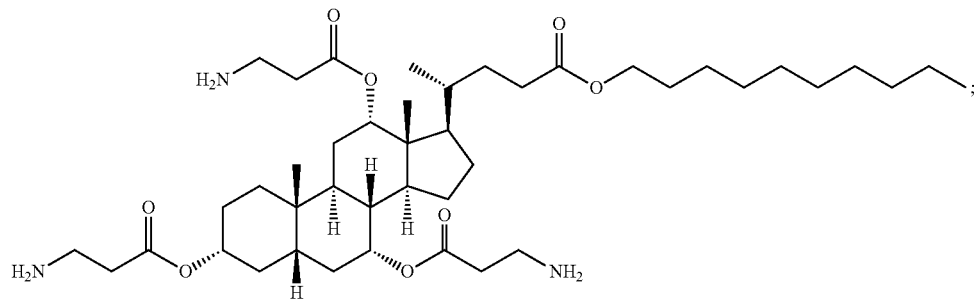
(CSA-144)
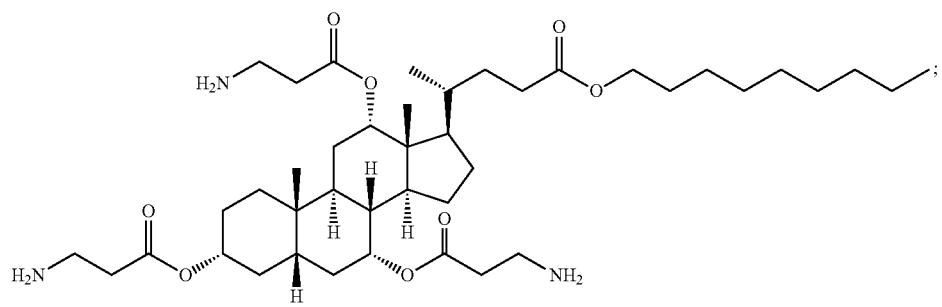
(CSA-145)
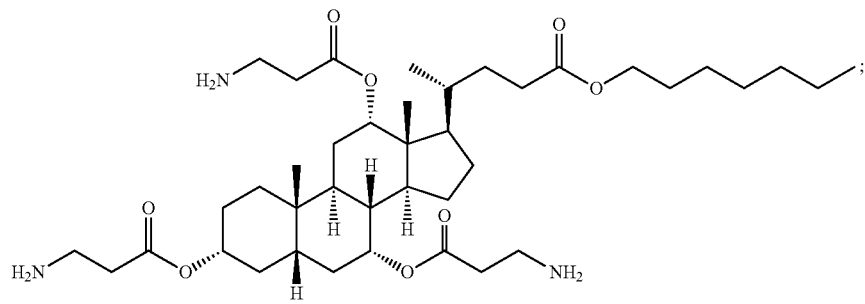
(CSA-146)
and pharmaceutically acceptable salt thereof.
27. A CSA-containing composition as in claim 25, wherein the compound of Formula (IB) or pharmaceutically acceptable salt thereof comprises:
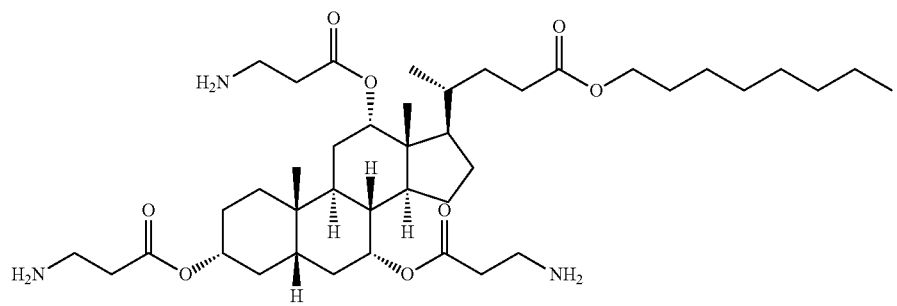
(CS-44)
or a pharmaceutically acceptable salt thereof.

28. A CSA-containing composition as in claim 12, wherein the pharmaceutically acceptable salt is a hydrochloride salt or a tri-hydrochloride salt.

29. A CSA-containing composition comprising:
a polar solvent or aqueous carrier;
a plurality of cationic steroidal antimicrobial (CSA) molecules; and
a micelle-forming agent comprising one or more surfactants having separate hydrophobic and hydrophilic regions,
the micelle-forming agent forming micelles encapsulating at least a portion of the CSA molecules so that at least about 75% of the CSA molecules are in the form of individually encapsulated particles less than 1 μm in size, and
wherein the CSA-containing composition maintains or increases efficacy in killing microbes and reduces or minimizes cytotoxicity to mammalian cells.

30. A CSA-containing composition as in claim 29, wherein the micelle-forming agent encapsulates at least a portion of the CSA molecules so that at least about 75% of the CSA molecules are in the form of individually encapsulated particles less than about 100 nm in size.

31. A CSA-containing composition as in claim 29, wherein the micelle-forming agent is selected from the group consisting of modified celluloses, modified nonionic hydroxyethyl cellulose, natural polyoxyethylene sorbitol ester, hydroxyethyl cellulose, 2-hydroxyethyl cellulose with a molecular weight between 90,000 and 750,000 and a viscosity between 50-500 cps in solutions between 1% and 5% water at temperatures between 20° C. and 25° C., modified aqueous solutions of polysorbate nonionic surfactants, polyoxyethylene sorbitan mono-, di-, and tri-($C_{12}$-$C_{18}$)-alkanoates, poloxamers, hydroxymethyl cellulose, ethyl cellulose, methyl cellulose, hydroxypropyl cellulose, carboxymethyl cellulose, alkyl triammonium methosulfate, and ceteraryloctanoate.

32. A CSA-containing composition comprising:
a polar solvent or aqueous carrier;
a plurality of cationic steroidal antimicrobial (CSA) molecules; and
a micelle-forming agent forming micelles encapsulating at least a portion of the CSA molecules so that no more than 25% of the CSA molecules form agglomerates larger than 500 nm in size, wherein the micelle-forming agent is selected from the group consisting of hydroxyethyl cellulose, polyoxyethylene sorbitol ester, modified aqueous solutions of polysorbate nonionic surfactants, polyoxyethylene sorbitan mono-, di-, and tri-($C_{12}$-$C_{18}$)-alkanoates, nonionic triblock copolymers composed of a central hydrophobic chain of polyoxypropylene (poly(propylene oxide)) flanked by two hydrophilic chains of polyoxyethylene (poly(ethylene oxide)), hydroxymethyl cellulose, ethyl cellulose, methyl cellulose, hydroxypropyl cellulose, carboxymethyl cellulose, alkyl triammonium methosulfate, ceteraryloctanoate, and combinations thereof,
wherein at least about 75% of the CSA molecules are in the form of individually sequestered particles less than 500 nm in size.

33. A CSA-containing composition as in claim 32, wherein the micelle-forming agent encapsulates at least a portion of the CSA molecules so that at least about 75% of the CSA molecules are in the form of individually sequestered particles less than about 100 nm in size.

34. A CSA-containing composition as in claim 32, wherein the micelle-forming agent is selected from the group consisting of 2 hydroxyethyl cellulose with a molecular weight between 90,000 and 750,000 and a viscosity between 50-500 cps in solutions between 1% and 5% water at temperatures between 20° C. and 25° C., nonionic triblock copolymers composed of a central hydrophobic chain of polyoxypropylene (poly(propylene oxide)) flanked by two hydrophilic chains of polyoxyethylene (poly(ethylene oxide)), hydroxymethyl cellulose, ethyl cellulose, methyl cellulose, hydroxypropyl cellulose, carboxymethyl cellulose, and combinations thereof.

* * * * *